(12) United States Patent
Szoka et al.

(10) Patent No.: US 7,723,472 B2
(45) Date of Patent: May 25, 2010

(54) EXTRACELLULAR MATRIX BINDING CHIMERIC PROTEINS AND METHODS OF USE THEREOF

(75) Inventors: Francis C. Szoka, San Francisco, CA (US); Joshua I. Park, San Francisco, CA (US); Robert Stull, Alameda, CA (US)

(73) Assignee: The Regents of the University of California, Oakland, CA (US)

( * ) Notice: Subject to any disclaimer, the term of this patent is extended or adjusted under 35 U.S.C. 154(b) by 416 days.

(21) Appl. No.: 11/365,073

(22) Filed: Feb. 28, 2006

(65) Prior Publication Data
US 2006/0239965 A1 Oct. 26, 2006

Related U.S. Application Data

(60) Provisional application No. 60/657,513, filed on Feb. 28, 2005.

(51) Int. Cl.
*C07K 5/00* (2006.01)

(52) U.S. Cl. .................................. 530/324; 530/350

(58) Field of Classification Search ................. 530/350, 530/324
See application file for complete search history.

(56) References Cited

U.S. PATENT DOCUMENTS

| | | | |
|---|---|---|---|
| 5,386,013 A | 1/1995 | Lee et al. | |
| 5,800,811 A | 9/1998 | Hall et al. | |
| 6,518,401 B1 | 2/2003 | Lee et al. | |
| 6,660,843 B1 | 12/2003 | Feige et al. | |
| 6,686,179 B2 | 2/2004 | Fleer et al. | |
| 2004/0234497 A1 | 11/2004 | Luo et al. | |
| 2005/0033026 A1 | 2/2005 | Corti et al. | |

OTHER PUBLICATIONS

Iczkowski et al (Antican. Res., 26:2863-2872. 2006).*
Jones (Pharmacogenomics Journal, 1:126-134, 2001).*
Tosatto et al (Current Pharmaceutical Design, 12:2067-2086, 2006).*
Skolnick et al. (Trends in Biotech, 18:34-39, 2000).*
Burgess et al. (J. Cell Bio., 111:2129-2138, 1990).*
Lazar et al. (Mol. Cell. Bio., 8:1247-1252, 1988).*
Guo et al. (PNAS, 101(25):9205-9210, 2004).*
Dougherty et al (JBC, 269(12):9074-9078, 1994).*
Aruffo et al., (1990), "CD44 Is the Principal Cell Surface Receptor for Hyaluronate", *Cell*, vol. 61, pp. 1303-1313.
Chang et al., (2003) "Fusion protein of the hyaluronan binding domain from human TSG-6 with luciferase for assay of hyaluronan", *Biotechnology Letters*, vol. 25, pp. 1037-1040.
Sy et al., (1992), "Inhibition of Tumor Growth In Vivo with a Soluble CD44-immunoglobulin Fusion Protein", *J. Exp. Med.*, vol. 176, pp. 623-627.

\* cited by examiner

*Primary Examiner*—Stephen L Rawlings
*Assistant Examiner*—Brad Duffy
(74) *Attorney, Agent, or Firm*—Paula A. Borden; Bozicevic, Field & Francis LLP

(57) ABSTRACT

The present invention provides chimeric polypeptides comprising a first polypeptide that binds to a component of extracellular matrix and a second polypeptide that provides for a therapeutic effect. The present invention further provides compositions, including pharmaceutical compositions, comprising a subject chimeric polypeptide. A subject chimeric polypeptide is useful in a variety of treatment, diagnostic, and research applications, which are also provided.

8 Claims, 12 Drawing Sheets

FIG. 1

Human CD44 amino acid sequence
NP_000601

```
  1 mdkfwwhaaw glclvplsla qidlnitcrf agvfhvekng rysisrteaa dlckafnstl
 61 ptmaqmekal sigfetcryg fieghvvipr ihpnsicaan ntgvyiltsn tsqydtycfn
121 asappeedct svtdlpnafd gpititivnr dgtryvqkge yrtnpediyp snptdddvss
181 gssserssts ggyifytfst vhpipdedsp witdstdrip attlmstsat atetatkrqe
241 twdwfswlfl psesknhlht ttqmagtssn tisagwepne enederdrhl sfsgsgiddd
301 edfisstist tprafdhtkg nqdwtqwnps hsnpevllqt ttrmtdvdrn gttayegnwn
361 peahpplihh ehheeeetph ststiqatps stteetatqk eqwfgnrwhe gyrqtpkeds
421 hsttgtaaas ahtshpmqgr ttpspedssw tdffnpishp mgrghqagrr mdmdsshsit
481 lqptanpntg lvedldrtgp lsmttqgsns qsfstshegl eedkdhptts tltssnrndv
541 tggrrdpnhs egsttllegy tshyphtkes rtfipvtsak tgsfgvtavt vgdsnsvnr
601 slsgdqdtfh psggshtthg sesdghshgs qegganttsg pirtpqipew liilasllal
661 alilavciav nsrrrcgqkk klvinsgnga vedrkpsgln geasksqemv hlvnkesset
721 pdgfmtadet rnlqnvdmki gv (SEQ ID NO:1)
```

FIG. 2

Human TSG6 amino acid sequence
GenBank accession no. NP_009046

```
  1 miiliylfll lwedtqgwgf kdgifhnsiw leraagvyhr earsgkyklt yaeakavcef
 61 egghlatykq leaarkigfh vcaagwmakg rvgypivkpg pncfgktgi  idygirlnrs
121 erwdaycynp hakecggvft dpkqifkspg fpneyednqi cywhirlkyg qrihlsfldf
181 dleddpgcla dyveiydsyd dvhgfvgryc gdelpddiis tgnvmtlkfl sdasvtaggf
241 qikyvamdpv skssqgknts ttstgnknfl agrfshl (SEQ ID NO:4)
```

Hyaluronan (HA)

glucuronic acid  N-acetylglucosamine

Conversion of 5-FC to 5-FU by GST-HBCD fusion protein

Conversion of cytosine to uracil

SEQUENCE LISTING

```
<160> NUMBER OF SEQ ID NOS: 14

<210> SEQ ID NO 1
<211> LENGTH: 742
<212> TYPE: PRT
<213> ORGANISM: H. sapiens

<400> SEQUENCE: 1

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220
```

```
Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
            245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
            275                 280                 285

His Leu Ser Phe Ser Gly Ser Gly Ile Asp Asp Glu Asp Phe Ile
290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
            325                 330                 335

Leu Leu Gln Thr Thr Thr Arg Met Thr Asp Val Asp Arg Asn Gly Thr
            340                 345                 350

Thr Ala Tyr Glu Gly Asn Trp Asn Pro Glu Ala His Pro Pro Leu Ile
            355                 360                 365

His His Glu His His Glu Glu Glu Thr Pro His Ser Thr Ser Thr
370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
            405                 410                 415

Lys Glu Asp Ser His Ser Thr Thr Gly Thr Ala Ala Ala Ser Ala His
            420                 425                 430

Thr Ser His Pro Met Gln Gly Arg Thr Thr Pro Ser Pro Glu Asp Ser
            435                 440                 445

Ser Trp Thr Asp Phe Phe Asn Pro Ile Ser His Pro Met Gly Arg Gly
450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
            485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
            515                 520                 525

Thr Ser Thr Leu Thr Ser Ser Asn Arg Asn Asp Val Thr Gly Gly Arg
530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
            565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
            595                 600                 605

Phe His Pro Ser Gly Gly Ser His Thr His Gly Ser Glu Ser Asp
            610                 615                 620

Gly His Ser His Gly Ser Gln Glu Gly Gly Ala Asn Thr Thr Ser Gly
625                 630                 635                 640
```

```
Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Lys Lys Lys Leu Val Ile Asn Ser Gly Asn
            675                 680                 685

Gly Ala Val Glu Asp Arg Lys Pro Ser Gly Leu Asn Gly Glu Ala Ser
    690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740

<210> SEQ ID NO 2
<211> LENGTH: 92
<212> TYPE: PRT
<213> ORGANISM: Artificial Sequence
<220> FEATURE:
<223> OTHER INFORMATION: synthetic fragment

<400> SEQUENCE: 2

Gly Val Phe His Val Glu Lys Asn Gly Arg Tyr Ser Ile Ser Arg Thr
1               5                   10                  15

Glu Ala Ala Asp Leu Cys Lys Ala Phe Asn Ser Thr Leu Pro Thr Met
            20                  25                  30

Ala Gln Met Glu Lys Ala Leu Ser Ile Gly Phe Glu Thr Cys Arg Tyr
        35                  40                  45

Gly Phe Ile Glu Gly His Val Val Ile Pro Arg Ile His Pro Asn Ser
    50                  55                  60

Ile Cys Ala Ala Asn Asn Thr Gly Val Tyr Ile Leu Thr Ser Asn Thr
65                  70                  75                  80

Ser Gln Tyr Asp Thr Tyr Cys Phe Asn Ala Ser Ala
            85                  90

<210> SEQ ID NO 3
<211> LENGTH: 93
<212> TYPE: PRT
<213> ORGANISM: Artificial Sequence
<220> FEATURE:
<223> OTHER INFORMATION: synthetic fragment

<400> SEQUENCE: 3

Gly Val Phe His Val Glu Lys Asn Gly Arg Tyr Ser Ile Ser Arg Thr
1               5                   10                  15

Glu Ala Ala Asp Leu Cys Gln Ala Phe Asn Ser Thr Leu Pro Thr Met
            20                  25                  30

Asp Gln Met Lys Leu Ala Leu Ser Lys Gly Phe Glu Thr Cys Arg Tyr
        35                  40                  45

Gly Phe Ile Glu Gly Asn Val Val Ile Pro Arg Ile His Pro Asn Ala
    50                  55                  60

Ile Cys Ala Ala Asn His Thr Gly Val Tyr Ile Leu Val Thr Ser Asn
65                  70                  75                  80

Thr Ser His Tyr Asp Thr Tyr Cys Phe Asn Ala Ser Ala
            85                  90

<210> SEQ ID NO 4
```

<211> LENGTH: 277
<212> TYPE: PRT
<213> ORGANISM: H. sapien

<400> SEQUENCE: 4

Met Ile Ile Leu Ile Tyr Leu Phe Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Gln
    130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Asp Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
        275

<210> SEQ ID NO 5
<211> LENGTH: 98
<212> TYPE: PRT
<213> ORGANISM: Artificial Sequence
<220> FEATURE:
<223> OTHER INFORMATION: synthetic fragment

<400> SEQUENCE: 5

Gly Val Tyr His Arg Glu Ala Arg Ser Gly Lys Tyr Lys Leu Thr Tyr
1               5                   10                  15

Ala Glu Ala Lys Ala Val Cys Glu Phe Glu Gly Gly His Leu Ala Thr
            20                  25                  30

Tyr Lys Gln Leu Glu Ala Ala Arg Lys Ile Gly Phe His Val Cys Ala
        35                  40                  45

```
Ala Gly Trp Met Ala Lys Gly Arg Val Gly Tyr Pro Ile Val Lys Pro
 50                  55                  60

Gly Pro Asn Cys Gly Phe Gly Lys Thr Gly Ile Ile Asp Tyr Gly Ile
 65                  70                  75                  80

Arg Leu Asn Arg Ser Glu Arg Trp Asp Ala Tyr Cys Tyr Asn Pro His
                 85                  90                  95

Ala Lys

<210> SEQ ID NO 6
<211> LENGTH: 12
<212> TYPE: PRT
<213> ORGANISM: Artificial Sequence
<220> FEATURE:
<223> OTHER INFORMATION: synthetic fragment

<400> SEQUENCE: 6

Gly Ala His Trp Gln Phe Asn Ala Leu Thr Val Arg
 1               5                  10

<210> SEQ ID NO 7
<211> LENGTH: 4
<212> TYPE: PRT
<213> ORGANISM: Artificial Sequence
<220> FEATURE:
<223> OTHER INFORMATION: synthetic linker

<400> SEQUENCE: 7

Gly Gly Gly Gly
 1

<210> SEQ ID NO 8
<211> LENGTH: 5
<212> TYPE: PRT
<213> ORGANISM: Artificial Sequence
<220> FEATURE:
<223> OTHER INFORMATION: synthetic linker

<400> SEQUENCE: 8

Gly Gly Gly Gly Gly
 1               5

<210> SEQ ID NO 9
<211> LENGTH: 8
<212> TYPE: PRT
<213> ORGANISM: Artificial Sequence
<220> FEATURE:
<223> OTHER INFORMATION: synthetic linker

<400> SEQUENCE: 9

Gly Gly Gly Lys Gly Gly Gly Gly
 1               5

<210> SEQ ID NO 10
<211> LENGTH: 8
<212> TYPE: PRT
<213> ORGANISM: Artificial Sequence
<220> FEATURE:
<223> OTHER INFORMATION: synthetic linker

<400> SEQUENCE: 10

Gly Gly Gly Asn Gly Ser Gly Gly
 1               5

<210> SEQ ID NO 11
<211> LENGTH: 8
```

```
<212> TYPE: PRT
<213> ORGANISM: Artificial Sequence
<220> FEATURE:
<223> OTHER INFORMATION: synthetic linker

<400> SEQUENCE: 11

Gly Gly Gly Cys Gly Gly Gly Gly
 1               5

<210> SEQ ID NO 12
<211> LENGTH: 20
<212> TYPE: PRT
<213> ORGANISM: Artificial Sequence
<220> FEATURE:
<223> OTHER INFORMATION: synthetic linker

<400> SEQUENCE: 12

Gly Gly Gly Gly Ser Gly Gly Gly Gly Ser Gly Gly Gly Gly Ser Gly
 1               5                  10                  15

Pro Asn Gly Gly
         20

<210> SEQ ID NO 13
<211> LENGTH: 4
<212> TYPE: PRT
<213> ORGANISM: Artificial Sequence
<220> FEATURE:
<223> OTHER INFORMATION: synthetic linker

<400> SEQUENCE: 13

Ser Gly Gly Gly
 1

<210> SEQ ID NO 14
<211> LENGTH: 6
<212> TYPE: PRT
<213> ORGANISM: Artificial Sequence
<220> FEATURE:
<223> OTHER INFORMATION: synthetic peptide

<400> SEQUENCE: 14

His His His His His His
 1               5
```

US 7,723,472 B2

EXTRACELLULAR MATRIX BINDING CHIMERIC PROTEINS AND METHODS OF USE THEREOF

CROSS-REFERENCE

This application claims the benefit of U.S. Provisional Patent Application No. 60/657,513, filed Feb. 28, 2005, which application is incorporated herein by reference in its entirety.

STATEMENT REGARDING FEDERALLY SPONSORED RESEARCH

This invention was made with government support under grant No. CA10726 awarded by the National Institutes of Health. The government has certain rights in this invention.

FIELD OF THE INVENTION

The present invention is in the field of chimeric proteins, and in particular chimeric proteins that bind an extracellular matrix component and that provide for a therapeutic effect.

BACKGROUND OF THE INVENTION

Ideal chemotherapeutic drugs against cancer would target and eradicate malignant cells while leaving normal cells intact, thus minimizing unwanted side effects of the treatment. Current drug therapy for cancer generally involves administering a cancer chemotherapeutic agent systemically, and affects both cancerous and normal cells. Recent developments in targeted therapies include monoclonal antibodies against growth factor receptors expressed on tumors to prevent cancer progression. While these target specific antibody drugs bring higher hopes for better disease management, only a small number of selected patients benefit from these treatments. This is because not all patients express the target proteins at high enough levels in tumors for the therapies to be effective.

Hyaluronan (HA) is a glycosaminoglycan found in all vertebrate tissues and body fluids. HA is composed of repeating N-acetyl-D-glucosamine and D-glucuronate disaccharide units, and its molecular weight ranges from $10^6$ to $10^7$. HA is synthesized by HA synthases (Has-1, Has-2, and Has-3 in humans), and the turnover rate in the body is high—less than 5 min in the blood, 1-2 days in the skin, and 1-3 weeks in cartilage. HA is digested by hyaluronidases (Hyals) that are found in circulating blood and tissues, and digested HA fragments can act as signaling molecules—high molecular weight HA can trigger anti-angiogenic and anti-inflammatory responses and low molecular weight HA (~20 kDa) can induce cytokine synthesis, whereas lower molecular weight HA (<20 kDa) can activate dendritic cells and antigen-presenting cells.

The altered regulation of HA seems to be important in tumor invasiveness, migration, and progression. Elevated levels of HA are found in various malignant tumors, including melanoma, and cancers of ovaries, breast, lung, and bladder. In breast and ovarian cancers, high HA levels are associated with poor patient survival. In addition, anchorage-independent growth and tumorigenicity were observed in hyaluronan synthase 2 (HAS-2) gene transfected human fibrosarcoma cells, which was correlated with overproduction of HA.

There is a need in the art for cancer treatments that provide for more targeted delivery of a therapeutic agent to a tumor. The present invention addresses this need; and provides related advantages.

Literature

U.S. Pat. Nos. 5,800,811, 660,843, and 6,686,179; U.S. Patent Publication Nos. 20050033026 and 20040234497.

SUMMARY OF THE INVENTION

The present invention provides chimeric polypeptides comprising a first polypeptide that binds to a component of extracellular matrix and a second polypeptide that provides for a therapeutic effect. The present invention further provides compositions, including pharmaceutical compositions, comprising a subject chimeric polypeptide. A subject chimeric polypeptide is useful in a variety of treatment, diagnostic, and research applications, which are also provided.

BRIEF DESCRIPTION OF THE DRAWINGS

FIG. 1 provides the amino acid sequence of a human CD44 protein.

FIG. 2 provides the amino acid sequence of a human TSG6 protein.

DEFINITIONS

Figure 3:
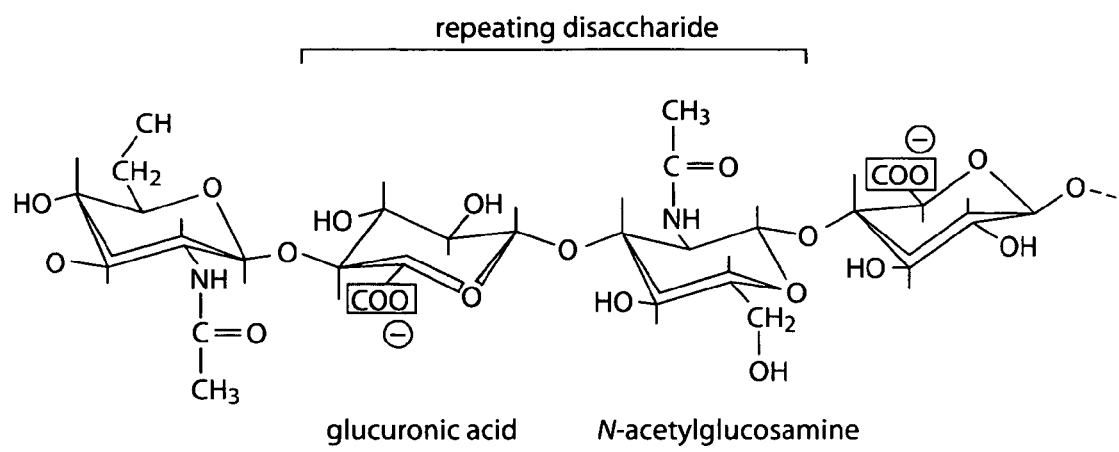
FIG. 3 depicts a structure of hyaluronan.
Figure 4:
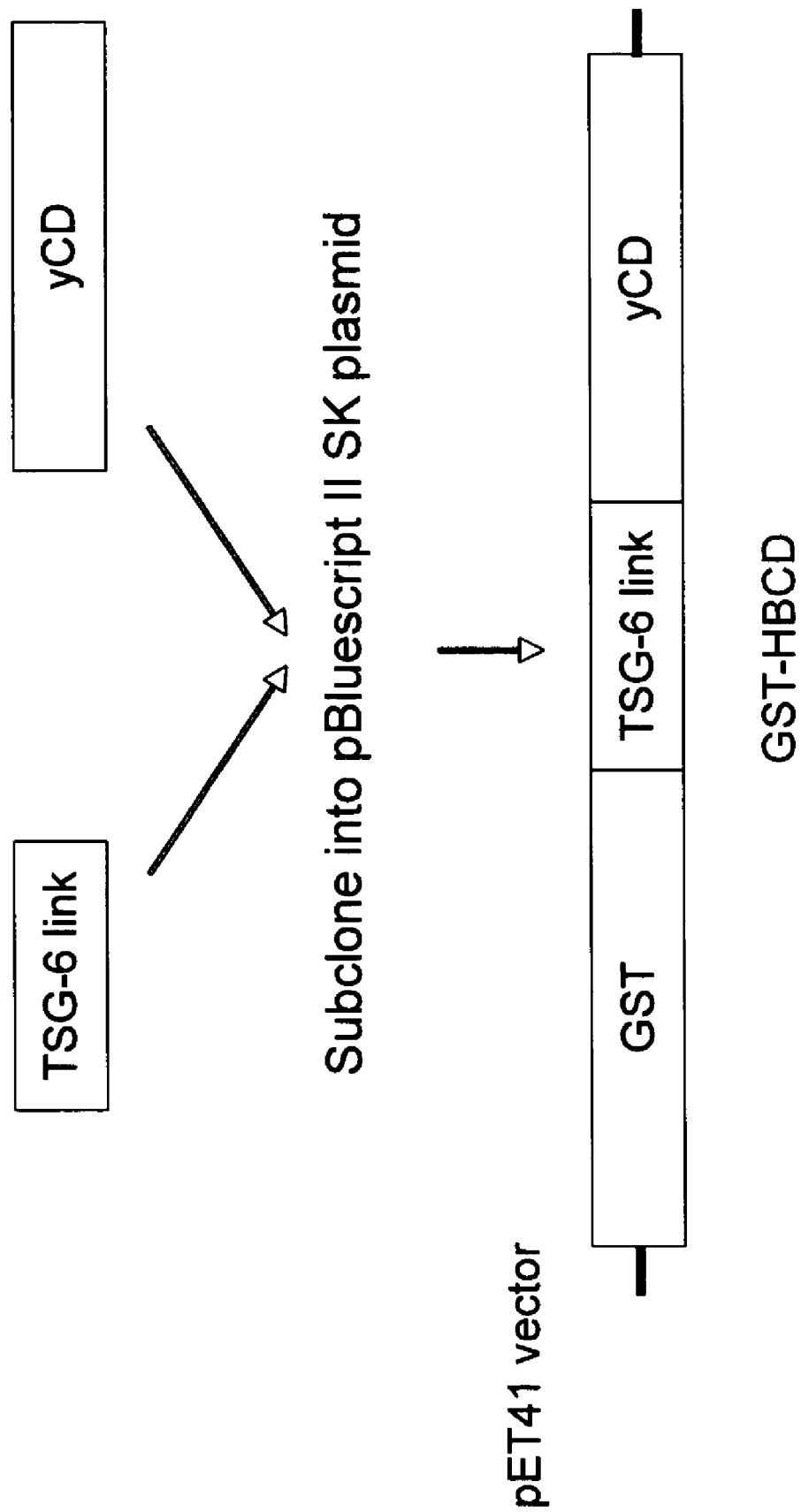
FIG. 4 depicts schematically a TSG-6 link-yeast cytosine deaminase fusion protein-encoding expression vector.

The terms "cancer," "neoplasm," and "tumor" are used interchangeably herein to refer to cells which exhibit relatively autonomous growth, so that they exhibit an aberrant growth phenotype characterized by a significant loss of control of cell proliferation. Cancerous cells can be benign or malignant.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O-5'-S-phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins (also referred to herein as "chimeric proteins" or "chimeric polypeptides"), including, but not limited to, fusion proteins with a heterologous amino acid sequence, fusions with heterologous and homologous leader sequences, with or without N-terminal methionine residues; immunologically tagged proteins; and the like.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "subject," "individual," "patient," and "host" are used interchangeably herein to refer to any subject for whom or which therapy is desired; these terms generally refer to the recipient of the therapy to be practiced according to the invention. The subject can be any vertebrate, but will typically be a mammal. If a mammal, the subject will in many embodiments be a human, but may also be a domestic livestock, laboratory subject or pet animal.

As used herein, "pharmaceutically acceptable carrier" includes any material which, when combined with an active ingredient of a composition, allows the ingredient to retain biological activity and without causing disruptive reactions with the subject's immune system. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed., Mack Publishing Col, Easton Pa. 18042, USA). Pharmaceutically acceptable excipients have been amply described in a variety of publications, including, for example, A. Gennaro (2000) "Remington: The Science and Practice of Pharmacy," 20th edition, Lippincott, Williams, & Wilkins; Remington's Pharmaceutical Sciences, 14th Ed. or latest edition, Mack Publishing Col, Easton Pa. 18042, USA; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a chimeric polypeptide" includes a plurality of such polypeptide and reference to "the therapeutic protein" includes reference to one or more therapeutic proteins and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides chimeric polypeptides comprising a first polypeptide that binds to a component of extracellular matrix and a second polypeptide that provides for a therapeutic effect. The present invention further provides compositions, including pharmaceutical compositions, comprising a subject chimeric polypeptide. A subject chimeric polypeptide is useful in a variety of treatment, diagnostic, and research applications, which are also provided.

Chimeric Polypeptides

The present invention provides chimeric polypeptides comprising a region that binds a component of the extracellular matrix (ECM), and a region that has biological activity, e.g., inhibits cell growth, inhibits angiogenesis, has an immunomodulatory effect, inhibits a matrix metalloproteinase, enhances nerve growth, enhances tissue regeneration, converts a prodrug to an active compound, and the like. The region that has biological activity is referred to herein interchangeably as "the therapeutic polypeptide" and "the biologically active polypeptide."

A subject chimeric polypeptide is useful for treating a disorder or condition that can be treated with the biologically active polypeptide. Thus, e.g., where the biologically active polypeptide is one that inhibits tumor growth, a subject chimeric polypeptide is useful for treating cancer; for diagnosing or imaging the site of a tumor; for monitoring the effect of the biologically active polypeptide in an experimental (non-human) animal model of cancer, etc. As another example, where the biologically active peptide is one that enhances tissue regeneration, subject chimeric polypeptide is useful for treating an individual in need of tissue regeneration (e.g., an individual suffering from Type 2 diabetes mellitus who exhibits areas of ischemia), etc.

A subject chimeric polypeptide is generally of the formula:

$$A\text{-}(X_1)_m\text{—}B\text{—}(X_2)_n\text{—}C, \text{ where:}$$

A and C, if present, are each flanking peptides;
B, if present, is a linker peptide;
$X_1$ is a first polypeptide that binds to a component of an extracellular matrix; and
$X_2$ is a second polypeptide that has therapeutic activity, where m and n are each independently an integer from 1 to 3.

In some embodiments, the positions of the first polypeptide ($X_1$) and the second polypeptide ($X_2$) are switched. In some embodiments, a subject chimeric polypeptide comprises a single ECM binding polypeptide. In other embodiments, a subject chimeric polypeptide comprises two or three ECM binding polypeptides. In some embodiments, a subject chimeric polypeptide comprises a single therapeutic polypeptide. In other embodiments, a subject chimeric polypeptide comprises two or three therapeutic polypeptides.

Flanking peptide A, if present, is also referred to as the amino-terminal flanking peptide. Flanking peptide C, if present, is also referred to as the carboxyl-terminal peptide. Each of A and C, if present, is independently from about 1 amino acid to about 300 amino acids in length, e.g., from about 1 amino acid to about 5 amino acids, from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, from about 40 amino acids to about 50 amino acids, from about 50 amino acids to about 60 amino acids, from about 60 amino acids to about 70 amino acids, from about 70 amino acids to about 80 amino acids, from about 80 amino acids to about 90 amino acids, from about 90 amino acids to about 100 amino acids in length, from about 100 amino acids to about 200 amino acids, or from about 200 amino acids to about 300 amino acids in length.

In some embodiments, one or more of the ECM binding polypeptide, the linker peptide (if present), the N-terminal flanking peptide (if present), and the C-terminal flanking peptide (if present) comprises a detectable label. Suitable detectable labels include, but are not limited to, enzymes such as alkaline phosphatase, β-galactosidase, peroxidase, microperoxidase, glucoseoxidase, glucose-6-phosphate dehydrogenase, malate dehydrogenase, and luciferase; a pigment such as Coomassie Brilliant Blue R250 and methyl orange; radioisotopes such as $^{99}$mTc, $^{131}$I, $^{125}$I, $^{14}$C, $^{3}$H, $^{32}$P and $^{35}$S;

fluorescent substances such as fluorescein, rhodamine, dansyl, fluorescamine, coumarin, naphthylamine, or derivatives thereof, fluorescent rare earth pigments [for example, a substance consisting of a combination of a rare earth metal such as samarium (Sm), europium (Eu), terbium (Tb) or dysprosium (Dy) and a chelate compound such as 4,4'-bis(1", 1",1",2",2",3",3"-heptafluoro-4",6"-hexanedion-6"-yl) chlorosulfo-o-terphenyl (BHHCT), 4,7-bis(chlorosulfonyl)-1, 10-phenanthroline-2,9-dicarboxylic acid (BCPDA), and β-naphthyltrifluoroacetic acid], and nucleic acid binding fluorescent pigments; luminescent substances such as luciferin, isoluminol, luminol and bis(2,4,6-trifluorophenyl) oxalate; substances having an absorption in the ultraviolet region such as phenol, naphthol, anthracene, or derivatives thereof; and substances having a property as a spin labeling agent represented by a compound having an oxyl group such as 4-amino-2,2,6,6-tetramethylpyperidine-1-oxyl, 3-amino-2,2,5,5-tetramethylpyrrolidine-1-oxyl, 2,6-di-t-butyl-α-(3, 5-di-t-butyl-4-oxo-2,5-cyclohexadiene-1-ylidene)-p-tolyloxyl; members of a specific binding pair, e.g., biotin (bound by avidin, streptavidin, etc.); and the like; a fluorescent dyes including e.g., coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc. Where a subject chimeric polypeptide is detectably labeled, a subject chimeric polypeptide is useful in various imaging methods, e.g., imaging a tumor to determine the extent or size of the tumor, etc.

Extracellular Matrix Binding Proteins

Extracellular matrix (ECM) binding proteins that are suitable for use in a subject chimeric polypeptide include, but are not limited to, binding proteins that bind to hyaluronan; binding proteins that bind to chondroitin sulfate; binding proteins that bind to heparin; and the like. In many embodiments, the ECM binding protein binds to a carbohydrate component of the ECM, e.g, binds a glycosaminoglycan, a sulfated glycosaminoglycan, etc. The ECM binding proteins will in some embodiments be full-length ECM binding proteins. In other embodiments, the ECM binding protein is an ECM binding fragment of an ECM binding protein.

Hyaluronan Binding Protein

In some embodiments, the extracellular matrix binding protein is a hyaluronan binding protein (HBP). Hyaluronan is composed of repeating N-acetyl-D-glucosamine and D-glucuronic acid units, as depicted in FIG. 3. HBP that are suitable for use in a subject chimeric polypeptide include, but are not limited to, a CD44 polypeptide, or hyaluronan-binding fragment or variant thereof; a TSG6 polypeptide, or hyaluronan-binding fragment or variant thereof; an HABP4 polypeptide, or hyaluronan-binding fragment or variant thereof; an HAPLN1 polypeptide, or hyaluronan-binding fragment or variant thereof; an RHAMM polypeptide, or hyaluronan-binding fragment or variant thereof; a STAB-1 polypeptide, or hyaluronan-binding fragment or variant thereof; a STAB-2 polypeptide, or hyaluronan-binding fragment or variant thereof; an XLKD1 polypeptide, or hyaluronan-binding fragment or variant thereof; a brevican polypeptide, or hyaluronan-binding fragment or variant thereof; an LYVE-1 polypeptide, or hyaluronan-binding fragment or variant thereof; an aggrecan polypeptide, or hyaluronan-binding fragment or variant thereof; a versican polypeptide, or hyaluronan-binding fragment or variant thereof; a neurocan polypeptide, or hyaluronan-binding fragment or variant thereof; and the like. In many embodiments, a hyaluronan-binding protein comprises a link module. See, e.g., Day and Prestwich (2002) *J. Biol. Chem.* 277:4585-4588.

CD44 polypeptides are known in the art. See, e.g., GenBank Accession No. NP_000601 for a human CD44 polypeptide amino acid sequence (and the nucleotide sequence of the encoding mRNA is found under GenBank Accession No. NM_000610); and AAA37407 for a mouse CD44 polypeptide amino acid sequence. Amino acid variants of CD44 that affect hyaluronan binding have been described. See, e.g., Bajorath et al. (1998) *J. Biol. Chem.* 273:338-343. A human TSG6 amino acid sequence is found under GenBank Accession No. NP_009046 (and an mRNA nucleotide sequence encoding human TSG6 is found under GenBank Accession No. NM_007115); a mouse TSG6 amino acid sequence is found under GenBank Accession No. NP_033424 (and corresponding mRNA sequence is found under GenBank Accession No. NM_009398). A human hyaluronan binding protein-4 (HABP4) amino acid sequence is found under GenBank Accession No. NP_055097 (and corresponding mRNA sequence is found under GenBank Accession No. NM_014282). A mouse HABP4 amino acid sequence is found under GenBank Accession No. AAH82806. A human hyaluronan and proteoglycan link protein-1 (HAPLN1) amino acid sequence is found under GenBank Accession No. NP_001875 (and corresponding mRNA sequence is found under GenBank Accession No. NM_001884). A human hyaluronan-mediated motility receptor (RHAMM) amino acid sequence is found under GenBank Accession No. NP_036616 (and corresponding mRNA sequence is found under GenBank Accession No. NM_012484). A human stabilin 1 (STAB1) amino acid sequence is found under GenBank Accession No. NP_055951 (and corresponding mRNA sequence is found under GenBank Accession No. NM_015136). A human stabilin 2 (STB2) amino acid sequence is found under GenBank Accession No. NP_060034 (and corresponding mRNA sequence is found under GenBank Accession No. NM_006691). A human extracellular link domain containing-1 (XLKD1) amino acid sequence is found under GenBank Accession No. NP_006682 (and corresponding mRNA sequence is found under GenBank Accession No. NM_006691). A human brevican amino acid sequence is found under GenBank Accession Nos. NP_068767 and NP_940819 (and corresponding mRNA sequences are found under GenBank Accession Nos. NM_021948 and NM_198427, respectively).

In some embodiments, a hyaluronan binding polypeptide comprises the amino acid sequence set forth in SEQ ID NO:1 and depicted in FIG. 1 (human CD44). In other embodiments, a hyaluronan binding polypeptide comprises the amino acid sequence: gvfhvekng rysisrteaa dlckafnstl ptmaqmekal sigfetcryg fieghvvipr ihpnsicaan ntgvyiltsn tsqydtycfn asa (SEQ ID NO:2; hyaluronan-binding fragment of human CD44). In other embodiments, a hyaluronan binding polypeptide comprises the amino acid sequence: gvfhv ekngrysisr teaadlcqaf nstlptmdqm klalskgfet crygfiegnv viprihpnai caanhtgvyi lvtsntshyd tycfnasa (SEQ ID NO:3; hyaluronan-binding fragment of mouse CD44).

In some embodiments, a hyaluronan binding polypeptide comprises the amino acid sequence set forth in SEQ ID NO:4 and depicted in FIG. 2 (human TSG6). In other embodiments, a hyaluronan-binding polypeptide comprises the amino acid sequence: gvyhr earsgkyklt yaeakavcef egghlatykq leaarkigfh vcaagwmakg rvgypivkpg pncgfgktgi idygirlnrs erwdaycynp hak (SEQ ID NO:5; hyaluronan-binding fragment of human TSG6).

In some embodiments, a hyaluronan binding polypeptide comprises a 12 amino acid synthetic peptide having the sequence GAHWQFNALTVR (SEQ ID NO:6) that binds to HA and that was identified using a phage display technique (Mummert M E, Mohamadzadeh M, Mummert D I, Mizumoto N, and Takashima A. Development of a peptide inhibitor of hyaluronan-mediated leukocyte trafficking. J. Exp. Med. 192:769-779, 2000).

Biologically Active Polypeptides

Biologically active polypeptides suitable for use in a subject chimeric polypeptide include, but are not limited to, enzymes that convert a prodrug into an active drug; immunomodulatory polypeptides; matrix metalloproteinase (MMP) inhibitors; angiogenesis inhibitors; chemoattractants; tissue growth factors; and the like.

Enzymes

Suitable enzymes that activate a prodrug, e.g., convert a prodrug into an active form include, but are not limited to, alkaline phosphatase for use in combination with phosphate-containing prodrugs (U.S. Pat. No. 4,975,278); arylsulfatase for use in combination with sulfate-containing prodrugs (U.S. Pat. No. 5,270,196); peptidases and proteases, such as serratia protease, thermolysin, subtilisin, carboxypeptidase (U.S. Pat. Nos. 5,660,829; 5,587,161; 5,405,990) and cathepsins (including cathepsin B and L), for use in combination with peptide-based prodrugs, e.g. MTX-α peptide (see, e.g., Hamstra and Rehemtulla (1999) *Gene Ther.* 10:235-248); D-alanylcarboxypeptidases for use in combination with D-amino acid-modified prodrugs; carbohydrate-cleaving enzymes such as β-galactosidase and neuraminidase for use in combination with glycosylated prodrugs (U.S. Pat. Nos. 5,561,119; 5,646,298); β-lactamase for use in combination with β-lactam-containing prodrugs; penicillin amidases, such as penicillin V amidase (U.S. Pat. No. 4,975,278) or penicillin G amidase, for use in combination with drugs derivatized at their amino nitrogens with phenoxyacetamide or phenylacetamide groups; β-glucuronidase, for use in combination with the prodrug HMR 1826 (Weyel et al. (2000) *Gene Ther.* 7:224-231); bacterial nitroreductase, for use in combination with the prodrug CB1954 (Friedlos et al. (1997) *J. Med. Chem.* 40:1270-1275); CYP2B1 and p450 reductase, for use in combination with cyclophosphamide (see, e.g., Chen et al. (1997) *Cancer Res.*: 57:4830-4837); thymidine phosphorylase, for use in combination with 5-fluorouridine or 5'-deoxy-5-fluorouridine (see, e.g., Evrard et al. (1999) *Br. J. Cancer* 80:1726-1733); β-galactosidase, for use in combination with anthracycline (see, e.g., Bakina and Farquhar (1999) *Anticancer Drug Des.* 14:507-515); thymidine kinase, for use in combination with ganciclovir (see, e.g., Vandier et al. (2000) *J. Natl. Cancer Inst.* 92:642-647; and cytosine deaminase (U.S. Pat. Nos. 5,338,678; 5,545,548) for use in combination with 5-fluorocytosine-based prodrugs (U.S. Pat. No. 4,975, 278).

In some embodiments, the enzyme is cytosine deaminase. The amino acid sequences of cytosine deaminase, as well as nucleotide sequences encoding same, are known in the art. For example, the amino acid sequence of yeast (*Saccharomyces cerevisiae*) cytosine deaminase is found under GenBank Accession No. NP_015387.

In some embodiments, the enzyme has at least 80%, at least 85%, at least 90%, at least 95%, or at least 98% amino acid sequence identity to a human cytidine deaminase that has been modified to catalyze the conversion of fluorocytosine to fluorouracil.

Immunomodulatory Polypeptides

Suitable immunomodulatory polypeptides include, but are not limited to, IL-2, IL-12, IFN-α, IFN-γ, IL-8, and IFN-β.

Suitable IFN-α include, but are not limited to, naturally-occurring IFN-α (including, but not limited to, naturally occurring IFN-α2a, IFN-α2b); recombinant interferon alpha-2b such as Intron-A interferon available from Schering Corporation, Kenilworth, N.J.; recombinant interferon alpha-2a such as Roferon interferon available from Hoffmann-La Roche, Nutley, N. J.; recombinant interferon alpha-2C such as Berofor alpha 2 interferon available from Boehringer Ingelheim Pharmaceutical, Inc., Ridgefield, Conn.; and interferon alpha-n1.

The term "IFN-α" also encompasses consensus IFN-α. Consensus IFN-α (also referred to as "CIFN" and "IFN-con" and "consensus interferon") encompasses but is not limited to the amino acid sequences designated IFN-con$_1$, IFN-con$_2$ and IFN-con$_3$ which are disclosed in U.S. Pat. Nos. 4,695,623 and 4,897,471; and consensus interferon as defined by determination of a consensus sequence of naturally occurring interferon alphas (e.g., Infergen®, InterMune, Inc., Brisbane, Calif.). IFN-con$_1$ is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods.

Also suitable for use in the present invention are fusion polypeptides comprising an IFN-α and a heterologous polypeptide. Suitable IFN-α fusion polypeptides include, but are not limited to, Albuferon-alpha™ (a fusion product of human albumin and IFN-α; Human Genome Sciences; see, e.g., Osborn et al. (2002) *J. Pharmacol. Exp. Therap.* 303: 540-548). Also suitable for use in the present invention are gene-shuffled forms of IFN-α. See., e.g., Masci et al. (2003) *Curr. Oncol. Rep.* 5:108-113.

Any of a variety of beta interferons can be used in a subject method. Suitable beta interferons include, but are not limited to, naturally-occurring IFN-β; IFN-β1a, e.g., Avonex® (Biogen, Inc.), and Rebif® (Serono, S A); IFN-β1b (Betaseron®; Berlex); and the like.

The nucleic acid sequences encoding IFN-gamma polypeptides may be accessed from public databases, e.g., Genbank, journal publications, and the like. While various mammalian IFN-gamma polypeptides are of interest, for the treatment of human disease, generally the human protein will be used. Human IFN-gamma coding sequence may be found in Genbank, accession numbers X13274; V00543; and NM_000619. The corresponding genomic sequence may be found in Genbank, accession numbers J00219; M37265; and V00536. See, for example. Gray et al. (1982) *Nature* 295:501 (Genbank X13274); and Rinderknecht et al. (1984) *J.B.C.* 259:6790.

IFN-γ1b (Actimmune®; human interferon) is a single-chain polypeptide of 140 amino acids. It is made recombinantly in *E. coli* and is unglycosylated (Rinderknecht et al. 1984, *J. Biol. Chem.* 259:6790-6797). Recombinant IFN-gamma as discussed in U.S. Pat. No. 6,497,871 is also suitable for use herein.

The IFN-gamma to be used in a subject chimeric polypeptide may be any of natural IFN-gamma, recombinant IFN-gamma and the derivatives thereof so far as they have an IFN-γ activity, particularly human IFN-gamma activity. Human IFN-gamma exhibits the antiviral and anti-proliferative properties characteristic of the interferons, as well as a number of other immunomodulatory activities, as is known in the art. Although IFN-gamma is based on the sequences as provided above, the production of the protein and proteolytic processing can result in processing variants thereof. The unprocessed sequence provided by Gray et al., supra, consists of 166 amino acids (aa). Although the recombinant IFN-gamma produced in *E. coli* was originally believed to be 146 amino acids, (commencing at amino acid 20) it was subsequently found that native human IFN-gamma is cleaved after residue 23, to produce a 143 aa protein, or 144 aa if the terminal methionine is present, as required for expression in bacteria. During purification, the mature protein can additionally be cleaved at the C terminus after reside 162 (referring to the Gray et al. sequence), resulting in a protein of 139 amino acids, or 140 amino acids if the initial methionine is present, e.g. if required for bacterial expression. The N-terminal methionine is an artifact encoded by the mRNA translational "start" signal AUG that, in the particular case of *E. coli* expression is not processed away. In other microbial systems or eukaryotic expression systems, methionine may be removed.

For use in a subject chimeric polypeptide, any of the native IFN-gamma peptides, modifications and variants thereof, or a combination of one or more peptides may be used. IFN-gamma peptides of interest include fragments, and can be variously truncated at the carboxyl terminus relative to the full sequence. Such fragments continue to exhibit the characteristic properties of human gamma interferon, so long as amino acids 24 to about 149 (numbering from the residues of the unprocessed polypeptide) are present. Extraneous sequences can be substituted for the amino acid sequence following amino acid 155 without loss of activity. See, for example, U.S. Pat. No. 5,690,925. Native IFN-gamma moieties include molecules variously extending from amino acid residues 24-150; 24-151, 24-152; 24-153, 24-155; and 24-157. Any of these variants, and other variants known in the art and having IFN-γ activity, may be used in a subject chimeric polypeptide.

The sequence of the IFN-gamma polypeptide may be altered in various ways known in the art to generate targeted changes in sequence. A variant polypeptide will usually be substantially similar to the sequences provided herein, i.e., will differ by at least one amino acid, and may differ by at least two but not more than about ten amino acids. The sequence changes may be substitutions, insertions or deletions. Scanning mutations that systematically introduce alanine, or other residues, may be used to determine key amino acids. Specific amino acid substitutions of interest include conservative and non-conservative changes. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. In one embodiment, the invention contemplates the use of IFN-gamma variants with one or more non-naturally occurring glycosylation and/or pegylation sites that are engineered to provide glycosyl- and/or PEG-derivatized polypeptides with reduced serum clearance, such as the IFN-gamma polypeptide variants described in International Patent Publication No. WO 01/36001 and WO 02/081507. Also included are modifications of glycosylation, e.g., those made by modifying the glycosylation patterns of a polypeptide during its synthesis and processing or in further processing steps; e.g., by exposing the polypeptide to enzymes that affect glycosylation, such as mammalian glycosylating or deglycosylating enzymes. Also embraced are sequences that have phosphorylated amino acid residues, e.g., phosphotyrosine, phosphoserine, or phosphothreonine.

Included for use are IFN-γ polypeptides that have been modified using ordinary chemical techniques so as to improve their resistance to proteolytic degradation, to optimize solubility properties, or to render them more suitable as a therapeutic agent. For examples, the backbone of the peptide may be cyclized to enhance stability (see, for example, Friedler et al. 2000, *J. Biol. Chem.* 275:23783-23789). Analogs may be used that include residues other than naturally occurring L-amino acids, e.g., D-amino acids or non-naturally occurring synthetic amino acids. The protein may be pegylated to enhance stability.

Matrix Metalloprotease Inhibitors

Matrix metalloproteinase (MMP) inhibitors that are suitable for use in a subject chimeric polypeptide include, but are not limited to, a tissue inhibitor of matrix metalloproteinase (TIMP), e.g., TIMP1, TIMP2, TIMP3, TIMP4, and the like. See, e.g., Woessner J. F., Faseb Journal, vol. 5, 1991, 2145.

The amino acid sequences of MMP inhibitors, as well as the nucleotide sequences of mRNA encoding same, are known in the art. For example, TIMP2 amino acid and mRNA sequences are found under GenBank Accession Nos. NP_003246 and NM_003255, respectively. TIMP4 amino acid and mRNA sequences are found under GenBank Accession Nos. NP_003247 and NM_003256, respectively. Amino acid sequences of human TIMP-1 and human TIMP-3 are found under GenBank Accession Nos. P01033 and P35625, respectively.

Angiogenesis Inhibitors

Angiogenesis inhibitors that are suitable for use in a subject chimeric polypeptide include, but are not limited to, a vascular endothelial growth factor (VEGF) antagonist, e.g., a soluble VEGF receptor; an anti-VEGF antibody; an anti-VEGF-receptor (anti-VEGFR) antibody; and the like.

Where the VEGF antagonist is an anti-VEGFR antibody, an anti-VEGFR antibody that is suitable for use in a subject method is one that specifically binds a VEGFR (e.g., VEGFR1 and/or VEGFR2), e.g., the antibody does not substantially bind to polypeptides that lack one or more epitopes displayed by a VEGFR. Similarly, an anti-VEGF antibody that is suitable for use herein is one that specifically binds VEGF, e.g., the antibody binds VEGF but does not substantially bind to polypeptides that lack one or more epitopes displayed by a VEGF. Typically, a specific antibody is one that binds VEGF or a VEGFR with an affinity of at least about $10^{-7}$ M, at least about $10^{-8}$ M, at least about $10^{-9}$ M, or at least about $10^{-10}$ M, or higher.

Exemplary non-limiting VEGF antagonists that are suitable for use include, but are not limited to, a monoclonal antibody to VEGF; a soluble VEGFR (see, e.g., Takayama et al. (2000) *Cancer Res.* 60:2169-2177; Mori et al. (2000) *Gene Ther.* 7:1027-1033; and Mahasreshti et al. (2001) *Clin. Cancer Res.* 7:2057-2066); a monoclonal antibody to VEGFR-2 (see, e.g., Prewett et al. (1999) *Cancer Res.* 59:5209-5218; Witte et al. (1998) *Cancer Metastasis Rev.* 17:155-161; Brekken et al. (2000) *Cancer Res.* 60:5117-5124; Kunkel et al. (2001) *Cancer Res.* 61:6624-6628); a soluble VEGFR as disclosed in U.S. Patent Publication No. 20030181377; an antibody to VEGFR as disclosed in U.S. Patent Publication No. 20030175271; a chimeric VEGF antagonist that includes an Ig domain from a VEGF receptor-1 (VEGFR1), an Ig domain from a VEGF receptor-2 (VEGFR2), and a dimerization domain or multimerization domain, as described in, e.g., Holash et al. ((2002) *Proc. Natl. Acad. Sci. USA* 99:11393-11398); and the like.

Growth Factors

In some embodiments, the biologically active polypeptide is a tissue growth factor. Suitable growth factors include Nerve Growth Factor (NGF), Basic Fibroblast Growth Factor (FGF) in its acid or basic forms, Ciliary Neurotrophic Factor (CNTF), Brain Derived Neurotrophic Factor (BDNF), Neurotrophin-3 (NT-3), vascular endothelial growth factor (VEGF), epidermal growth factor (EGF), transforming growth factor-α (TGF-α), leukemia inhibitory factor 7; platelet derived growth factor; and Neurotrophin-4 (NT-4). Also suitable are GM-CSF, G-CSF, and other colony stimulating factors. Also suitable is stromal derived factor-1. Also suitable are bone morphogenetic proteins (BMP) such as native or recombinant human BMP-2, BMP-3 (osteogenin), BMP-4 and BMP-7 (OP-1, osteogenetic protein-1).

In some embodiments, the biologically active polypeptide is a neurotrophic factor selected from: nerve growth factor (NGF), brain-derived neurotrophic factor (BDNF), cardiotrophin-1 (CT-1), choline acetyltransferase development factor (CDF), ciliary neurotrophic factor (CNTF), oncostatin M (OSM); glial cell-line-derived neurotrophic factor (GDNF), insulin, insulin-like growth factor-1 (IGF-1), IGF-2, interleukin-6 (IL-6), leukemia inhibitor factor (LIF), neurite promoting factor (NPF), neurotrophin-3 (NT-3), NT-4, platelet-derived growth factor (PDGF), protease nexin-1 (PN-1), S-100, transforming growth factor-β (TGF-β) and vasoactive intestinal peptide (VIP).

Flanking Polypeptides

Flanking polypeptides A and C, if present at all, will generally each independently have a length of from about one to about 300 amino acids, e.g., from about one amino acid to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to abut 40 amino acids, from about 40 amino acids to about 50 amino acids, from about 50 amino acids to about 60 amino acids, from about 60 amino acids to about 70 amino acids, from about 70 amino acids to about 80 amino acids, from about 80 amino acids to about 100 amino acids, from about 100 amino acids to about 125 amino acids, from about 125 to about 150 amino acids, from about 150 amino acids to about 200 amino acids, from about 200 amino acids to about 250 amino acids, or from about 250 amino acids to about 300 amino acids.

Suitable flanking polypeptides include, but are not limited to, therapeutic polypeptides; epitope tags (a hemagglutinin tag, a FLAG tag, and the like); polypeptides that provide for ease of purification (e.g., glutathione-S-transferase; a metal binding polypeptide such as a poly(His) tract (e.g., $His_6$ SEQ ID NO:14) and the like); polypeptides that provide a secretion signal for secretion from a eukaryotic cell or a prokaryotic cell; polypeptides that provide for increased serum half life; albumin; an immunoglobulin fragment, e.g., an immunoglobulin Fc portion; an antigen-binding fragment of an antibody; and the like.

Linkers

As noted above, the presence of any "linker" group ("B") is optional. When present, its chemical structure is not critical. A linker, if present, serves primarily as a spacer. The linker is typically made up of amino acids linked together by peptide bonds. Thus, in some embodiments, the linker is made up of from 1 to 50 amino acids linked by peptide bonds, e.g., from about 1 amino acid to about 3 amino acids, from about 3 amino acids to about 5 amino acids, from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, or from about 40 amino acids to about 50 amino acids. Generally, the amino acids are selected from the 20 naturally occurring amino acids. Some of these amino acids may be glycosylated, as is well understood by those in the art. In one embodiment, the 1 to 50 amino acids are selected from glycine, alanine, proline, asparagine, glutamine, seine, and lysine. In some embodiments, a linker is made up of a majority of amino acids that are sterically unhindered, such as glycine and alanine. Combinations of seine and glycine also make suitable linkers. Thus, exemplary linkers are polyglycines (particularly $(Gly)_4$ (SEQ ID NO:7), $(Gly)_5$ (SEQ ID NO:8)), poly(Gly-Ala), and polyalanines. Other specific examples of linkers are: $(Gly)_3$ Lys $(Gly)_4$ (SEQ ID NO:9); $(Gly)_3$AsnGlySer$(Gly)_2$ (SEQ ID NO:10); $(Gly)_3$Cys$(Gly)_4$ (SEQ ID NO:11); $[(Gly)_4Ser]3$ GlyProAsnGlyGly (SEQ ID NO:12); GlySerGly; SerGlyGly; SerGlyGlyGly (SEQ ID NO:13); and the like. Non-peptide linkers are also possible.

Modifications

One or more of the ECM binding polypeptide, the biologically active polypeptide, and the optional flanking polypeptides of a subject chimeric polypeptide will in some embodiments be a variant polypeptide, e.g., a polypeptide that differs in amino acid sequence from a corresponding naturally-occurring polypeptide, or from another reference polypeptide. A variant polypeptide will usually be substantially similar to the sequences provided herein, i.e. will differ by at least one amino acid, and may differ by at least two but generally not more than about ten amino acids. The sequence changes may be substitutions, insertions or deletions. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylananine, tyrosine).

Modifications of interest that may or may not alter the primary amino acid sequence of a polypeptide include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

A polypeptide will in some embodiments include one or more modifications designed to modify one or more properties such as half-life, solubility, resistance to proteolytic degradation, and the like, without substantially decreasing the biological activity of the polypeptide. Such modifications include, but are not limited to, addition of one or more biocompatible polymers, such as polyethylene glycol (PEG) moieties (e.g., "PEGylation", where the modified polypeptide is referred to as a "PEGylated" polypeptide); glycosylation; phosphorylation; and acetylation.

Compositions

The present invention provides compositions, including pharmaceutical compositions, comprising a subject chimeric polypeptide. The present invention also provides compositions, including pharmaceutical compositions, comprising a subject polynucleotide, e.g., a subject recombinant vector. Compositions will typically include a subject chimeric polypeptide or a subject polynucleotide; and one or more of a buffer (e.g., a Tris buffer, a phosphate buffer, HEPES, etc.), a salt (NaCl, $MgCl_2$, a magnesium salt, sodium phosphate, potassium phosphate, etc.), a detergent (e.g., a non-ionic detergent), a solubilizing agent (e.g., dimethylsulfoxide), a pH adjusting agent, a chelating agent (e.g., EDTA, EGTA, etc.), a preservative (e.g., sodium azide, glycerol, etc.); and the like. A carbohydrate such as sucrose, lactose, trehalose, maltose, mannitol, lacitol, sorbitol, and the like, to add in lyophilization of the chimeric polypeptide. Pharmaceutical compositions are described in more detail below.

In many embodiments, a subject chimeric polypeptide or a subject polynucleotide is present in a subject composition in substantially pure form, e.g., the subject chimeric polypeptide is at least about 80% pure, at least about 85% pure, at least about 90% pure, at least about 95% pure, at least about 98% pure, at least about 99% pure, or greater than 99% pure.

Methods of Making a Subject Chimeric Polypeptide

A subject chimeric polypeptide is generally made in transformed host cells using recombinant DNA techniques. To do so, a recombinant DNA molecule coding for the subject chimeric polypeptide is prepared. Methods of preparing such DNA molecules are well known in the art. For instance, sequences coding for the subject chimeric polypeptide could be excised from DNA using suitable restriction enzymes. Alternatively, the DNA molecule could be synthesized using chemical synthesis techniques, such as the phosphoramidate method. Also, a combination of these techniques could be used.

A subject chimeric polypeptide may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941, 763; Finn et al. (1976), The Proteins (3rd ed.) 2: 105-253; and Erickson et al. (1976), The Proteins (3rd ed.) 2: 257-527.

Polynucleotides, Vectors, and Host Cells

The present invention further provides polynucleotides, and compositions comprising the polynucleotides (e.g., "nucleic acid compositions"), which polynucleotides comprise a nucleotide sequence that encodes a subject chimeric polypeptide. By nucleic acid composition is meant a composition comprising a sequence of DNA having an open reading frame that encodes one the subject chimeric polypeptide and is capable, under appropriate conditions, of being expressed as one of the subject chimeric polypeptides described above. Thus, the term encompasses genomic DNA, cDNA, mRNA, and vectors comprising the subject nucleic acids.

Nucleic acids encoding the proteins and polypeptides of the subject invention may be cDNA or genomic DNA or a fragment thereof. The term gene shall be intended to mean the open reading frame encoding specific proteins and polypeptides of the subject invention, and introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a protein according to the subject invention.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject proteins. Double or single stranded fragments may be obtained from the DNA sequence by chemically synthesizing oligonucleotides in accordance with conventional methods, by restriction enzyme digestion, by PCR amplification, etc.

The subject nucleic acids may also be provided as part of a vector (e.g., a chimeric polypeptide-encoding construct), a wide variety of which are known in the art and need not be elaborated upon herein. Thus, the present invention provides a recombinant vector comprising a subject nucleic acid. Vectors include, but are not limited to, plasmids; cosmids; viral vectors; artificial chromosomes (YAC's, BAC's, etc.); mini-chromosomes; and the like. Vectors are amply described in numerous publications well known to those in the art, including, e.g., Short Protocols in Molecular Biology, (1999) F. Ausubel, et al., eds., Wiley & Sons. Vectors may provide for expression of the subject nucleic acids, may provide for propagating the subject nucleic acids, or both.

Vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Alternatively, recombinant virus vectors may be engineered, including but not limited to those derived from viruses such as herpes virus, retroviruses, vaccinia virus, poxviruses, adenoviruses, adeno-associated viruses or bovine papilloma virus.

The subject nucleic acid compositions find use in the preparation of all or a portion of the chimeric polypeptides of the subject invention, as described above. For expression, an expression cassette may be employed. Thus, the present invention provides a recombinant expression vector comprising a subject nucleic acid. The expression vector will provide a transcriptional and translational initiation region, which may be inducible or constitutive, where the coding region is operably linked under the transcriptional control of the transcriptional initiation region, and a transcriptional and translational termination region. These control regions may be native to a gene encoding the subject peptides, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, luciferase; a fluorescent protein, e.g., green fluorescent protein, etc.

Expression cassettes may be prepared comprising a transcription initiation region, the gene or fragment thereof, and a transcriptional termination region. After introduction of the DNA, the cells containing the construct may be selected by means of a selectable marker, the cells expanded and then used for expression.

Proteins and polypeptides may be expressed in prokaryotes or eukaryotes in accordance with conventional ways, depending upon the purpose for expression. Thus, the present invention further provides a host cell, e.g., a genetically modified host cell, that comprises a subject polynucleotide, or a subject recombinant vector.

For large scale production of the protein, a unicellular organism, such as *E. coli, B. subtilis, S. cerevisiae*, insect cells in combination with baculovirus vectors, or cells of a higher organism such as insects, vertebrates,particularly mammals, e.g. COS 7 cells, may be used as the expression host cells. In some situations, it is desirable to express the gene in eukaryotic cells, where the encoded protein will benefit from native folding and post-translational modifications. Small peptides can also be synthesized in the laboratory. Polypeptides that are subsets of the complete sequences of the subject proteins may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433;

DeBoer et al., *Proc. Natl. Acad. Sci. (USA)* (1983) 80:21-25; and Siebenlist et al., *Cell* (1980) 20:269.

Yeast. Expression systems in yeast include those described in Hinnen et al., *Proc. Natl. Acad. Sci. (USA)* (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1 165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284-289; Tilburn et al., *Gene* (1983) 26:205-221; Yelton et al., *Proc. Natl. Acad. Sci. (USA)* (1984) 81:1470-1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409; Maeda et al., *Nature* (1985) 315:592-594; Lebacq-Verheyden et al., *Mol. Cell. Biol.* (1988) 8:3129; Smith et al., *Proc. Natl. Acad. Sci. (USA)* (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594.

Mammalian Cells. Mammalian expression is accomplished as described in Dijkema et al., *EMBO J.* (1985) 4:761, Gorman et al., *Proc. Natl. Acad. Sci. (USA)* (1982) 79:6777, Boshart et al., *Cell* (1985) 41:521 and U.S. Pat. No. 4,399, 216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

A subject chimeric polypeptide may be obtained from naturally occurring sources or synthetically produced. For example, the chimeric polypeptide may be derived from biological sources which express the proteins. The subject chimeric polypeptide may also be derived from synthetic means, e.g. by expressing a recombinant gene encoding protein of interest in a suitable host, as described in greater detail infra. Any convenient protein purification procedures may be employed, where suitable protein purification methodologies are described in Guide to Protein Purification, (Deuthser ed.) (Academic Press, 1990). For example, a lysate may prepared from a cell comprising the expression vector expressing the subject chimeric polypeptide, and purified using HPLC, exclusion chromatography, gel electrophoresis, affinity chromatography, and the like.

Utility

A subject chimeric polypeptide is useful in a variety of research, diagnostic, and therapeutic applications, which use will depend, in part, on the nature of the second polypeptide (e.g., the biologically active polypeptide). A subject polynucleotide is useful for producing a subject chimeric polypeptide, both in vitro and in vivo. In some embodiments, a subject polynucleotide is introduced into a subject, such that the polynucleotide enters a eukaryotic cell in the subject and the encoded chimeric polypeptide is produced. A subject polynucleotide is thus useful in a variety of research, diagnostic, and therapeutic applications, which use will depend, in part, on the nature of the second polypeptide (e.g., the biologically active polypeptide).

For research applications, a subject chimeric polypeptide is useful for identifying portions of an ECM binding polypeptide that are effective in targeting a subject chimeric polypeptide to a particular tumor; for identifying portions of a biologically active polypeptide that effect a particular biological activity; for determining the efficacy of a subject chimeric polypeptide against various tumor types; for determining the efficacy of a subject chimeric polypeptide in inhibiting angiogenesis; etc.

Therapeutic applications of a subject chimeric polypeptide or a subject polynucleotide will depend, in part, on the nature of the biologically active (second) polypeptide. Therapeutic methods include cancer treatment, nerve regeneration, and tissue regeneration.

Cancer Treatments

In some embodiments, the present invention provides a method of reducing tumor load, a method of reducing tumor mass, and a method of reducing the rate of tumor growth, the methods generally involving administering to an individual having a tumor an effective amount of a subject chimeric polypeptide. In some embodiments, a subject method for reducing tumor load, reducing tumor mass, or reducing the rate of tumor growth further involves administering an effective amount a second chemotherapeutic agent, administering radiation treatment, or subjecting the patient to a surgical method for reducing tumor mass. In some of these embodiments, a subject chimeric polypeptide comprises, as the biologically active polypeptide, an enzyme that converts a prodrug to a cytotoxic cancer chemotherapeutic agent. In some of these embodiments, a subject chimeric polypeptide comprises, as the biologically active polypeptide, a polypeptide that is a chemoattractant for natural killer (NK) cells, such as IL-8. In some of these embodiments, a subject chimeric polypeptide comprises, as the biologically active polypeptide, an immunomodulatory polypeptide selected from IL-2, IL-12, IFN-α, IFN-β, and IFN-γ.

The methods are effective to reduce a tumor load by at least about 5%, at least about 10%, at least about 20%, at least about 25%, at least about 50%, at least about 75%, at least about 85%, or at least about 90%, up to total eradication of the tumor, when compared to a suitable control. Thus, in these embodiments, "effective amounts" of a subject chimeric polypeptide is an amount that is sufficient to reduce tumor load by at least about 5%, at least about 10%, at least about 20%, at least about 25%, at least about 50%, at least about 75%, at least about 85%, or at least about 90%, up to total eradication of the tumor, when compared to a suitable control. In an experimental animal system, a suitable control may be the tumor load present in a genetically identical animal not treated with the subject chimeric polypeptide therapy. In non-experimental systems, a suitable control may be the tumor load present before administering the subject chimeric polypeptide therapy. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen) to determine the number of cells bearing a given tumor antigen; computed tomography scanning, magnetic resonance imaging, and/or x-ray imaging of the tumor to estimate and/or monitor tumor size; measuring the amount of tumor-associated antigen in a biological sample, e.g., blood; and the like.

In some embodiments, a subject method for reducing tumor load, reducing tumor mass, or reducing the rate of tumor growth further involves administering an effective amount of a prodrug, e.g., where the biologically active polypeptide is an enzyme that converts a prodrug to an active anti-cancer drug. In some embodiments, the enzyme is cytosine deaminase (CD) and the prodrug is 5-FC (5-fluorocytosine). In these embodiments, an effective amount of a subject chimeric polypeptide is an amount that, in combination with a prodrug, is effective to reduce tumor mass by at least about 10%, by at least about 15%, by at least about 20%, by at least about 25%, by at least about 30%, by at least about 35%, by at least about 40%, by at least about 50%, by at least about 60%, by at least about 70%, by at least about 80%, by at least about 90%, or more, up to total eradication of the tumor.

The methods are effective to reduce the growth rate of a tumor by at least about 5%, at least about 10%, at least about 20%, at least about 25%, at least about 50%, at least about 75%, at least about 85%, or at least about 90%, up to total inhibition of growth of the tumor, when compared to a suitable control. Thus, in these embodiments, an "effective amounts" of a subject chimeric polypeptide is an amount that is sufficient to reduce tumor growth rate by at least about 5%, at least about 10%, at least about 20%, at least about 25%, at least about 50%, at least about 75%, at least about 85%, or at least about 90%, up to total inhibition of tumor growth, when compared to a suitable control. In an experimental animal system, a suitable control may be the growth rate of a tumor in a genetically identical animal not treated with the subject chimeric polypeptide therapy. In non-experimental systems, a suitable control may be the growth rate of a tumor observed before administering the subject chimeric polypeptide therapy. Other suitable controls may be a placebo control.

Whether growth of a tumor is inhibited can be determined using any known method, including, but not limited to, an in vitro proliferation assay such as a $^3$H-thymidine uptake assay, and the like.

The methods are useful for treating a wide variety of cancers, including carcinomas, sarcomas, leukemias, and lymphomas. In many embodiments, the cancer being treated using a subject method is a solid tumor.

In some embodiments, the present invention provides a method of reducing tumor load, a method of reducing tumor mass, and a method of reducing the rate of tumor growth, the methods generally involving administering to an individual having a tumor an effective amount of a subject polynucleotide. In some embodiments, a subject method for reducing tumor load, reducing tumor mass, or reducing the rate of tumor growth further involves administering an effective amount a chemotherapeutic agent, administering radiation treatment, or subjecting the patient to a surgical method for reducing tumor mass. In some of these embodiments, the subject polynucleotide comprises a nucleotide sequence that encodes a subject chimeric polypeptide comprising, as the biologically active polypeptide, an enzyme that converts a prodrug to a cytotoxic cancer chemotherapeutic agent. In some of these embodiments, the subject polynucleotide comprises a nucleotide sequence that encodes a subject chimeric polypeptide comprising, as the biologically active polypeptide, a polypeptide that is a chemoattractant for natural killer (NK) cells, such as IL-8. In some embodiments, the subject polynucleotide comprises a nucleotide sequence that encodes a subject chimeric polypeptide comprising, as the biologically active polypeptide, an immunomodulatory polypeptide selected from IL-2, IL-12, IFN-$\alpha$, IFN-$\beta$, and IFN-$\gamma$.

A subject polynucleotide is delivered to a subject using any known method. Such methods include adenovirus-mediated delivery; lentivirus-mediated delivery; adeno-associated virus-mediated delivery; delivery of naked polynucleotides; delivery of polypeptides to the bloodstream via oral delivery (see, e.g., U.S. Pat. No. 6,831,070). The polynucleotide may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; and the like.

Tissue Regeneration

The present invention further provides methods of increasing nerve growth in an individual in need thereof, the method generally involving administering to the individual an effective amount of a subject chimeric polypeptide, or a subject polynucleotide encoding a subject polypeptide, where the second polypeptide portion is a nerve growth factor.

The present invention further provides methods of enhancing tissue repair in an individual in need thereof, the methods generally involving administering to the individual an effective amount of a subject chimeric polypeptide, or a subject polynucleotide encoding a subject polypeptide, where the biologically active polypeptide is selected from: a chemoattractant for cells involved in tissue repair; a colony stimulating factor (e.g., granulocyte/macrophage-colony stimulating factor (GM-CSF), granulocyte-colony stimulating factor (G-CSF), stromal derived factor-1, vascular endothelial growth factor, basic fibroblast growth factor (bFGF), epidermal growth factor (EGF), and the like.

In some embodiments, a subject chimeric polypeptide, or a subject polynucleotide is administered to the central nervous system (CNS) of a subject using convection-enhanced delivery (CED). CED can be conducted, for example, using either an osmotic pump or an infusion pump.

Any convection-enhanced delivery device may be appropriate for delivery of a subject polynucleotide or a subject polypeptide. In a preferred embodiment, the device is an osmotic pump or an infusion pump. Both osmotic and infusion pumps are commerically available from a variety of suppliers, for example Alzet Corporation, Hamilton Corporation, Alza, Inc., Palo Alto, Calif.). Typically, a subject polypeptide or a subject polynucleotide is delivered via CED devices as follows. A catheter, cannula or other injection device is inserted into central nervous system (CNS) tissue in the chosen subject. One of skill in the art could readily determine which general area of the CNS is an appropriate target. Stereotactic maps and positioning devices are available, for example from ASI Instruments, Warren, Mich. Positioning may also be conducted by using anatomical maps obtained by CT and/or MRI imaging of the subject's brain to help guide the injection device to the chosen target. Moreover, because the methods described herein can be practiced such that relatively large areas of the brain take up the subject polypeptide or subject polynucleotid, fewer infusion cannula are needed. Since surgical complications are related to the number of penetrations, the methods described herein also serve to reduce the side effects seen with conventional delivery techniques.

Dosages, Formulations, and Routes of Administration

Active agents (e.g., a subject chimeric polypeptide) are generally administered to individuals in formulations admixed with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H.C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods, the active agents may be administered to the host using any convenient means capable of resulting in the desired therapeutic effect. Thus, the active agents can be incorporated into a variety of formulations for therapeutic administration. More particularly, the active agents can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways. Conventional and pharmaceutically acceptable routes of administration include, but are not necessarily limited to, intramuscular, subcutaneous, intradermal, transdermal, intravenous, intratumoral, peritumoral, rectal (e.g., enema, suppository), oral, intragastric, intranasal and other routes of effective inhalation routes, and other parenteral routes of administration. Routes of administration may be combined, if desired, or adjusted depending upon the therapeutic agent. The active agent (e.g., a subject chimeric polypeptide) can be administered in a single dose or in multiple doses, and may encompass administration of additional doses, to elicit and/or maintain the desired effect.

An active agent can be administered to a subject using any available conventional methods and routes suitable for delivery of conventional drugs, including systemic or localized routes. Methods and localized routes that further facilitate activity of the active agent, particularly at or near a site of inflammation is of interest in the invention, and may be preferred over systemic routes of administration, both for the immediacy of therapeutic effect and reduction of the incident of in vivo degradation of the administered active agent. In general, routes of administration contemplated by the invention include, but are not necessarily limited to, gastroenteral, enteral, or parenteral routes. Gastroenteral routes of administration include, but are not necessarily limited to, oral and rectal (e.g., using a suppository) delivery. In some embodiments, the active agent is delivered at, near, or into a tumor, e.g., the administration is intratumoral or peritumoral.

Subcutaneous administration of an active agent is accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of a subject chimeric polypeptide to a patient through the port is referred to herein as "a subcutaneous injection port delivery system." In some embodiments, subcutaneous administration is achieved by a combination of devices, e.g., bolus delivery by needle and syringe, followed by delivery using a continuous delivery system.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the agents can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent calculated in an amount sufficient to produce the desired effect in association with a pharmaceutically acceptable diluent, carrier or vehicle. The specifications for the dosage form depend on the particular compound employed and the effect to be achieved, and the pharmacodynamics associated with each compound in the host.

The dose of an active agent administered to a subject, in the context of the present invention, should be sufficient to effect a beneficial therapeutic response in the subject over time, or to alleviate symptoms. Thus, an active agent is administered to a patient in an amount sufficient to alleviate, reduce, cure or at least partially arrest symptoms and/or complications from the disease. An amount adequate to accomplish this is defined as a "therapeutically effective dose."

In general, a subject chimeric polypeptide is administered to an individual in an amount of from about 5 µg to about 1200 mg, e.g., from about 5 µg to about 10 µg, from about 10 µg to about 50 µg, from about 50 µg to about 100 µg, from about 100 µg to about 500 µg, from about 500 µg to about 1 mg, from about 1 mg to about 10 mg, from about 10 mg to about 50 mg, from about 50 mg to about 100 mg, from about 100 mg to about 250 mg, from about 250 mg to about 500 mg, from about 500 mg to about 1000 mg, or from about 1000 mg to about 1200 mg.

In many embodiments, a subject chimeric polypeptide is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. A subject chimeric polypeptide can be administered tid, bid, qd, qod, biw, tiw, qw, qow, three times per month, once monthly, substantially continuously, or continuously.

In many embodiments, multiple doses of a subject chimeric polypeptide are administered. For example, a subject chimeric polypeptide is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Combination Therapies

In some embodiments, the present invention provides methods for combination therapy using a subject chimeric polypeptide, where the subject chimeric polypeptide is administered as adjuvant therapy to a primary cancer therapy. Primary cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and TAXOL®(paclitaxel) derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the invention include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ (8) colony-stimulating factors; and (9) inhibitors of angiogenesis.

Pharmaceuticals Compositions and Kits

The present invention provides pharmaceutical compositions comprising a subject chimeric polypeptide; and a pharmaceutically acceptable excipient. In some embodiments, a subject pharmaceutical composition further comprises at least one additional therapeutic agent (e.g., a cancer chemotherapeutic agent).

Pharmaceutical compositions comprising a subject chimeric polypeptide can be provided in a wide variety of formulations. More particularly, the subject chimeric polypeptide can be formulated into pharmaceutical compositions by combination with appropriate, pharmaceutically acceptable carriers or diluents, and may be formulated into preparations in solid, semi-solid (e.g., gel), liquid or gaseous forms, such as tablets, capsules, powders, granules, ointments, solutions, suppositories, injections, inhalants and aerosols.

The subject chimeric polypeptide can be formulated into preparations for injection by dissolving, suspending or emulsifying it in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

For oral preparations, the subject chimeric polypeptide can be used by itself or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The subject chimeric polypeptide can be made into suppositories by mixing with a variety of bases such as emulsifying bases or water-soluble bases. The subject chimeric polypeptide can be administered rectally via a suppository or enema. The suppository can include vehicles such as cocoa butter, carbowaxes and polyethylene glycols, which melt at body temperature, yet are solidified at room temperature.

Kits with unit doses of the subject chimeric polypeptide, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

In such kits, in addition to the containers containing the unit doses will be an informational package insert describing the use agent(s) in treating a disorder, e.g., a cancer. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, compact disc (CD), etc., on which the information has been recorded. Other suitable media include audiovisual media, e.g., digital versatile disk (DVD), videotape, and the like. Yet another means that may be present is a website address which may be used via the Internet to access the information at a removed site. Any convenient means may be present in the kits.

The present invention provides a medication delivery device pre-loaded with a therapeutically effective amount of a subject chimeric polypeptide, e.g., a sufficient amount for one bolus injection of the subject chimeric polypeptide, in the treatment of a patient suffering from a cancer, a patient in need of tissue repair, or a patient in need of nerve regeneration. In some embodiments, the medication delivery device is a syringe and needle, pre-loaded with a dosage of a subject chimeric polypeptide.

In other embodiments, the medication delivery device is a pen injector (e.g., a medication delivery pen), a number of which are known in the art. Exemplary devices which can be adapted for use in the present methods are any of a variety of pen injectors from Becton Dickinson, e.g., BDTM Pen, BDTM Pen II, BDTM Auto-Injector; a pen injector from Innoject, Inc.; any of the medication delivery pen devices discussed in U.S. Pat. Nos. 5,728,074, 6,096,010, 6,146,361, 6,248,095, 6,277,099, and 6,221,053; and the like. The medication delivery pen can be disposable, or reusable and refillable.

In other embodiments, the medication delivery device is an implantable drug delivery system, preferably a system that is programmable to provide for subcutaneous administration of a subject chimeric polypeptide. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

Subjects Suitable for Treatment

Individuals suitable for treatment with a subject treatment method for treating a cancer (e.g., methods for reducing tumor mass, etc.) include individuals suffering from a cancer, particularly individuals having a solid tumor; individuals who have undergone a previous treatment for the cancer, but who have failed such treatment; and individuals who have undergone a previous treatment for the cancer, who initially responded, but who subsequently relapsed, e.g., the tumor was initially in remission, but subsequently recurred.

Individuals suitable for treatment with a subject treatment method for inducing nerve growth and/or tissue regeneration include individuals suffering from a disorder or condition that would benefit from such treatment, including, but not limited to, periodontitis; a chronic nervous system injury resulting from physical transection/trauma, contusion/compression or surgical lesion, vascular pharmacologic insults including hemorrhagic or ischemic damage, or from neurodegenerative or other neurological diseases; neurodegenerative diseases including autoimmune and/or inflammatory diseases; wounds, e.g., an ischemic wound, a burn wound, and the like; etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Cloning, Protein Purification, and Functional Characterization of Fusion Protein Commercially available cDNA of CD44 (American Type Culture Collection) and yCD cytosine deaminase; Invivogen) were used to construct an HBD-yCD (hyaluronan binding domain-cytosine deaminase) fusion gene and inserted into pET4 expression vector (Novagen) containing a glutathione-S-transferase (GST) tag for protein expression in *E.coli* cells (Table 1).

TABLE 1

List of fusion proteins expressed and purified from *E. coli*

| Protein | Mw (monomer) | Description |
|---------|--------------|-------------|
| HBD-yCD | 39 kDa | Hyaluronan binding domain of soluble CD44-yeast cytosine deaminase |
| mtHBD-yCD | 39 kDa | Functional mutant (R41A) of HBD-yeast cytosine deaminase |
| yCD | 17 kDa | Yeast cytosine deaminase |

A functional point mutant of the CD44 protein is also made using site-directed mutagenesis to replace Arg 41 residue with Ala, which reduces the protein's affinity to hyaluronan (HA) (Bajorath 1998). Protein purification was performed by affinity column chromatography using glutathione-SEPHAROSE® (agarose) beads. The GST tag was removed by enterokinase, and the desired protein was further purified by size-exclusion chromatography.

To characterize the function of HBD-yCD and mtHBD-yCD proteins, in vitro assays were performed to measure HA binding activities and 5-FC→5-FU catalytic activities. HA binding assay with biotinylated-HA was adapted from Teriete et. al. (2004). High-performance liquid chromatography (HPLC)-UV detection of 5-FC and 5-FU was adapted from Wallace, et. al. (1994) and Torano, et. al (2001) to determine $K_m$ and $V_{max}$ of the fusion proteins and compare those numbers with the published values for yCD ($K_m$ 0.8 mM and $V_{max}$ 68 µM/min/µg enzyme, Kievit, et. al. 1999).

Figure 5:
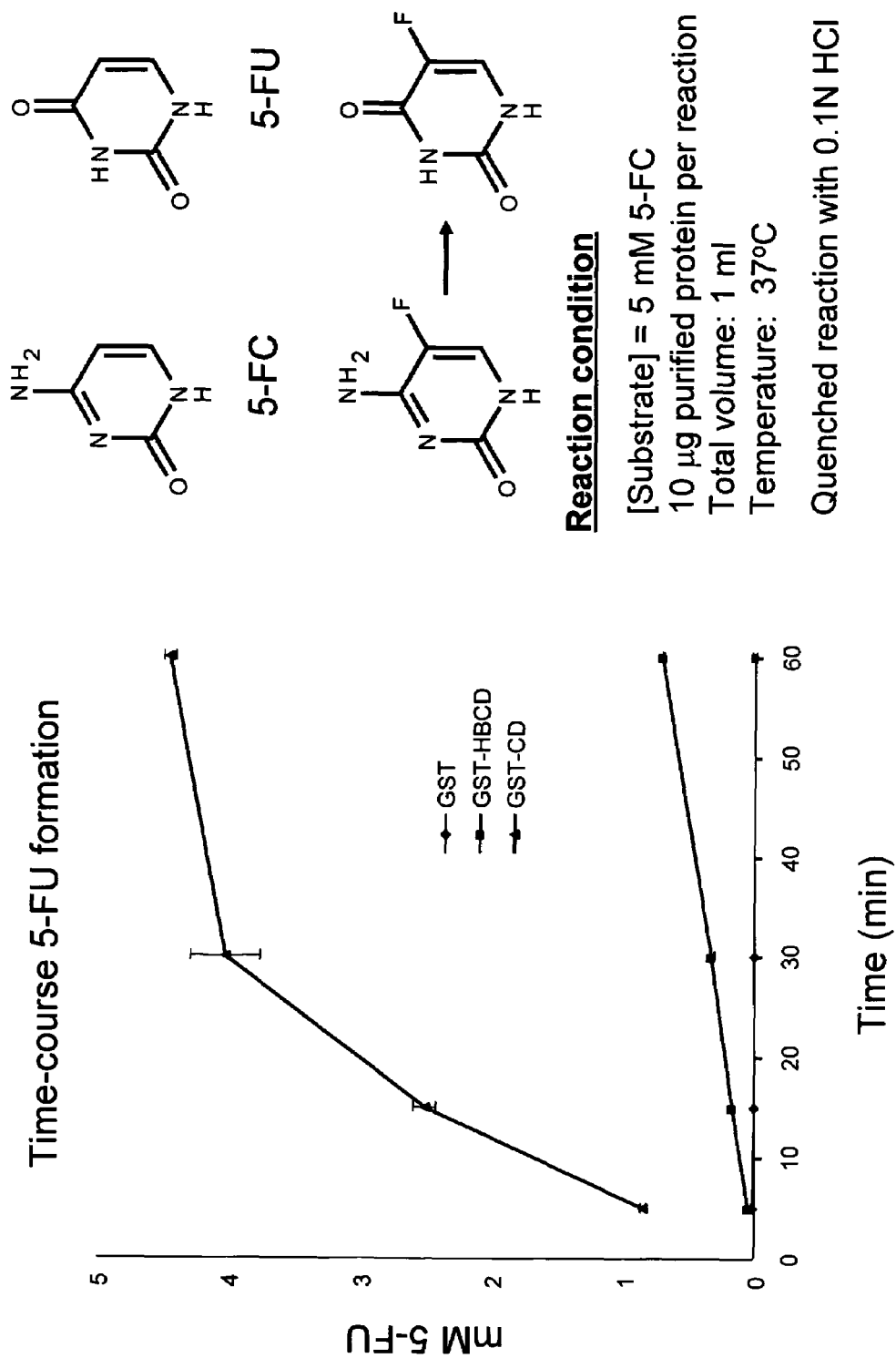
FIG. 5 depicts conversion of 5-FC to 5-FU by a GST-HBCD fusion protein.
Figure 6:
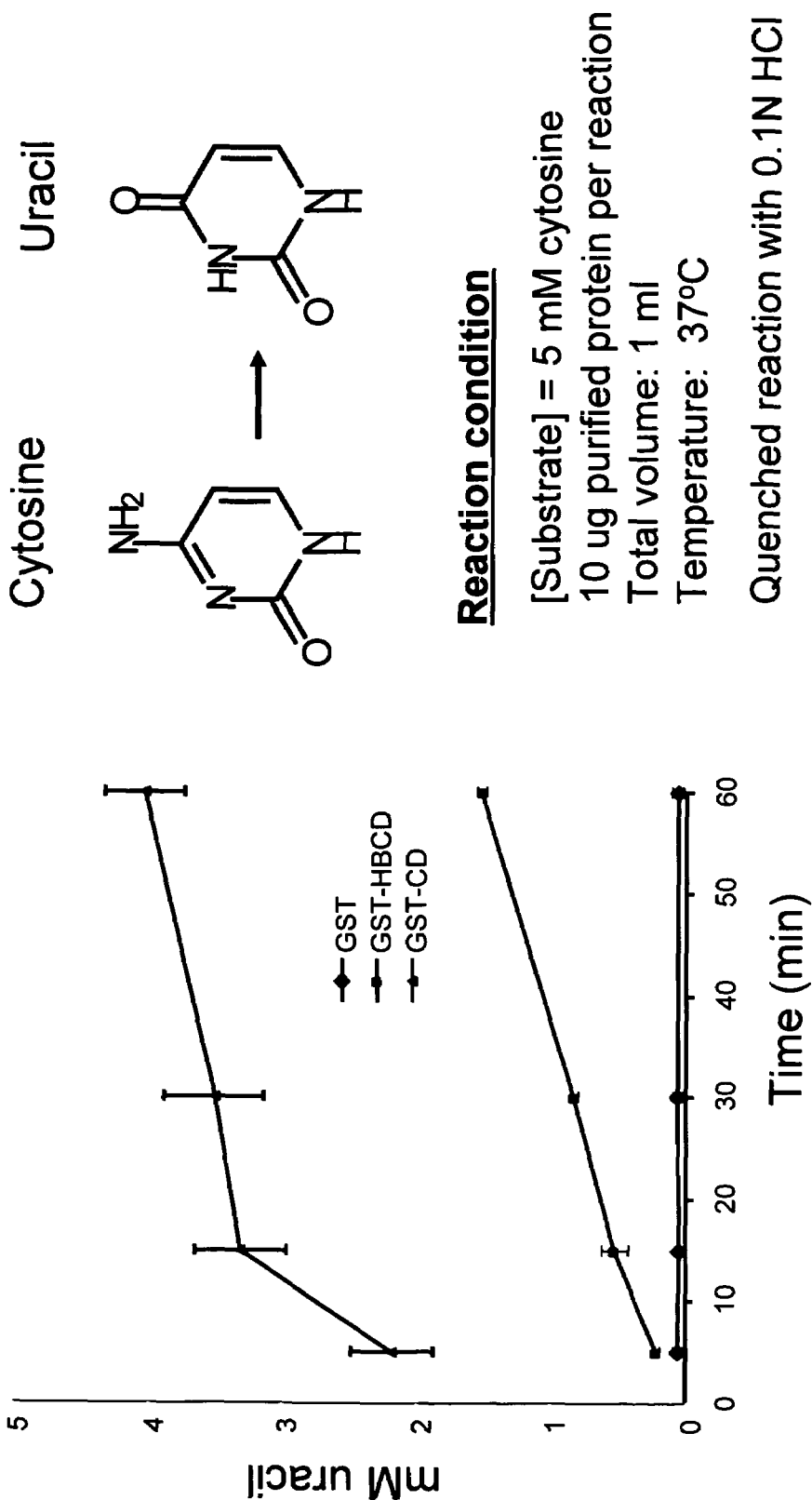
FIG. 6 depicts conversion of cytosine to uracil.
Figure 7:
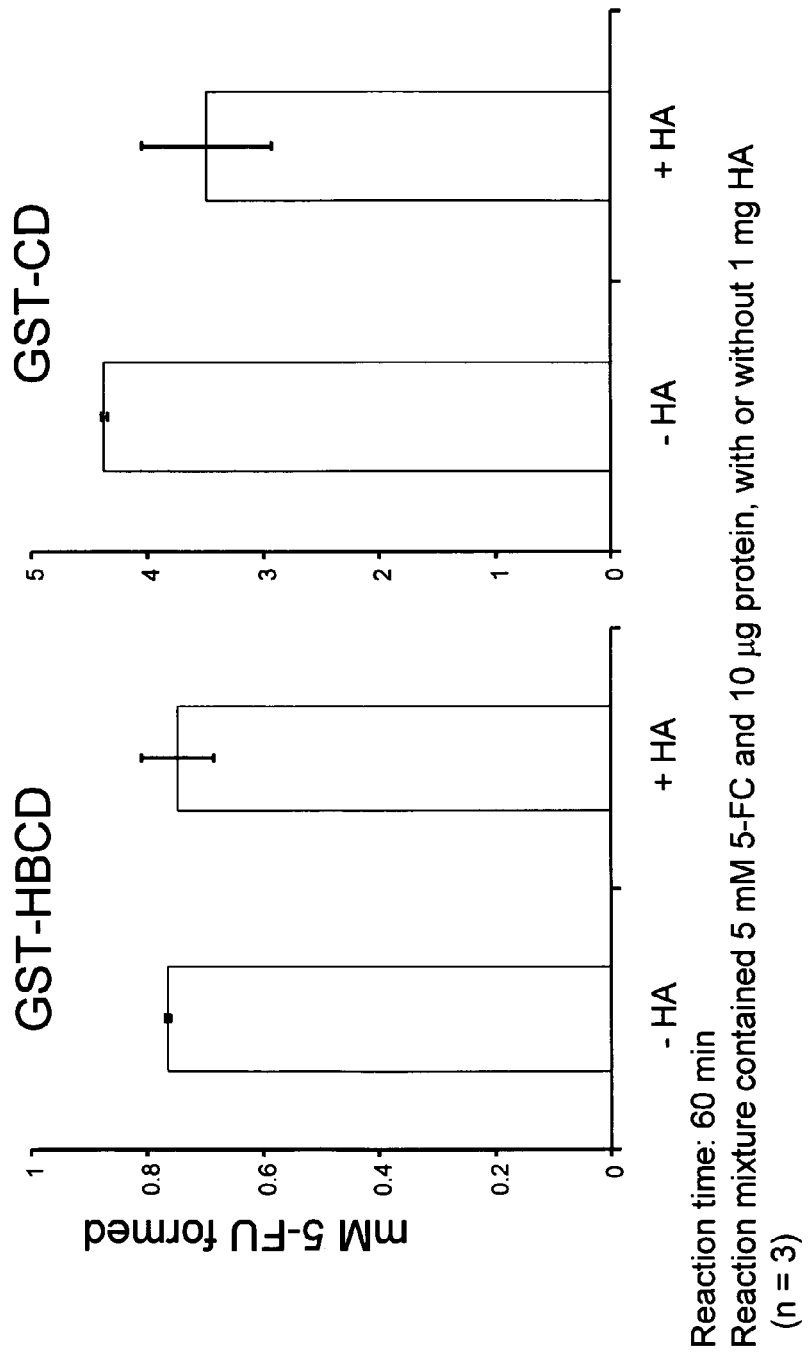
FIG. 7 depicts the effect on conversion of 5-FC to 5-FU by GST-HBCD and GST-CD.
Figure 8:
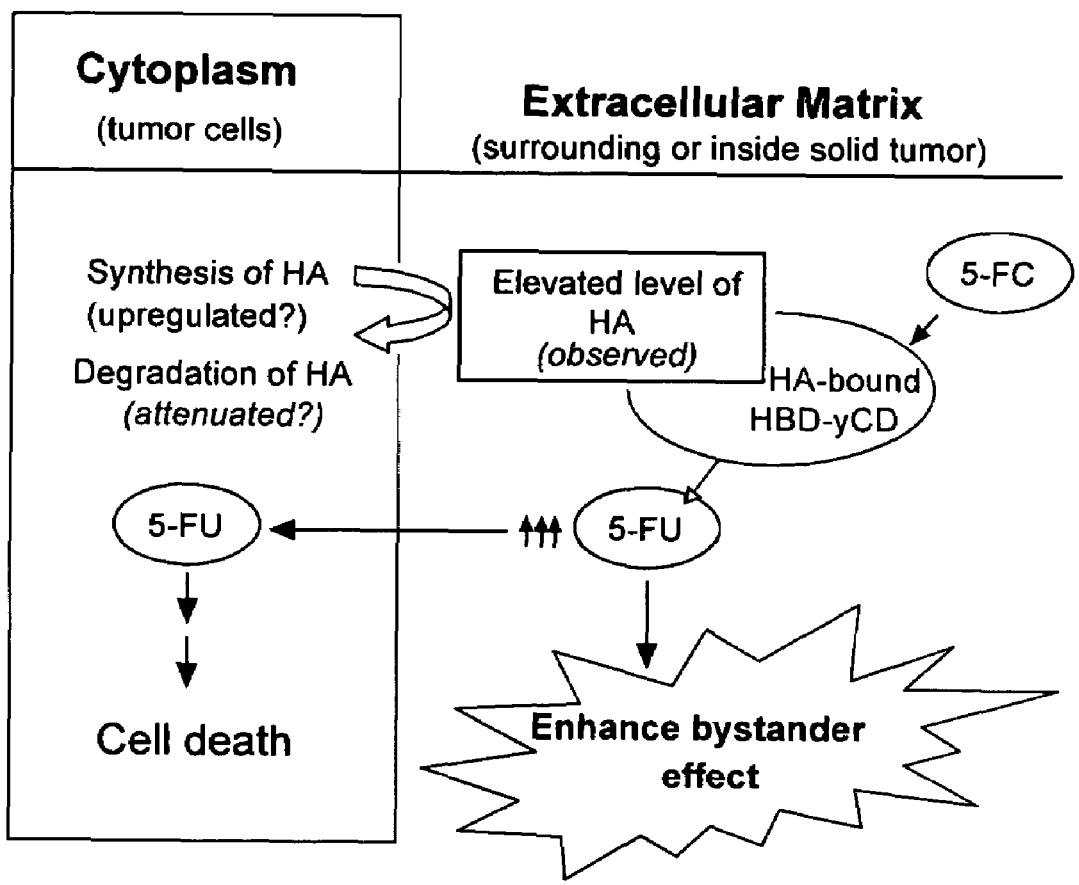
FIG. 8 is a schematic depiction of an exemplary embodiment of the present invention for targeting hyaluronan-rich tumor using a subject chimeric protein (hyaluronan-binding protein/yeast cytosine deaminase; HBD-yCD).

The HBD-yCD ("GST-HBCD") chimeric protein converted 5-FC to 5-FU. The results are shown in FIGS. 5-7. Data are shown for GST alone, GST-hyaluronan binding domain-cytidine deaminase (GST-HBDCD) chimeric protein, and GST-CD fusion protein Example 2

Biodistribution and Pharmacokinetics of 125I Radio-Labeled Proteins In Vivo in Human Breast Tumor-Bearing SCID Mice To determine the biodistribution of the HBD-yCD fusion protein in severe combined immunodeficiency (SCID) mice (with and without tumor); and to determine whether the chimeric protein accumulation occurs in the HA-rich tumor region, a mouse breast cancer model is used. A human breast tumor model is established in BALB/c SCID mice using MCF-7 cells. MCF-7 cells have been shown to produce abundant HA and metastasize in BALB/c SCID mice (Jojovic et. al. 2002). $10^7$ viable MCF-7 cells are subcutaneously injected SCID mice to form solid tumor, and the tumor size is measured daily. HBD-yCD, mtHBD, and yCD are radio-labeled with $^{125}I$ (specific activity of $10^{10}$ cpm/mg), and the radio labeled protein is injected SCID mice (with and without tumor) via tail vein injection (e.g., 300 µg/25 g mouse). At various time points, blood and urine are collected to measure iodo-protein content. From these data, the half-life ($t_{1/2}$), clearance (CL), volume of distribution (V), and AUC (Area Under the Curve) of the labeled protein are calculated.

In addition, various organs and tumor are removed to measure the weight and radio activity in these organs at different time points. Sections of solid tumor are examined using detectably labeled HBD to determine the level of HA.

Pharmacokinetic parameters of 5-FC and 5-FU (CL, $t_{1/2}$, V, bioavailability (F), and AUC) in SCID mice are determined after tail-vein and intraperitoneal (i.p.) injections. Plasma concentration of 5-FC are determined using HPLC-UV method (Wallace, et. al. 1994 and Torano, et. al. 2001).

After HBD-yCD/5FC treatment, blood samples, tumor mass, and major organs are collected at various time points (30 min to 5 hr) for measuring 5-FC and 5-FU with HPLC. The 5-FC/5-FU ratio in tumors is compared to that of blood and other organs.

The procedure is repeated with different amounts of 5-FC dose to achieve high level of prodrug conversion (i.e., less 5-FC/5-FU ratio) in the tumor, while the 5-FC/5-FU ratio is high and the presence of 5-FU in the blood and other organs stay low. Tumor size reduction is measured daily to evaluate the efficacy of the HBD-yCD/5-FC treatment.

Example 3

Construction of *E.coli* Expression Vector Containing GST-TSG6Link-yCD Fusion Gene The cDNA of human TSG was purchased from American Type Culture Collection. The Link domain of TSG (amino acid residues 36 to 133; SEQ ID NO:5) gene was amplified by PCR and subcloned into pBlueScript II SK plasmid (Stratagene). The TSGLink gene was then ligated into pET41 *E.coli* expression vector (Novagen) containing the Glutathione-S-Transferase (GST) gene at the N-terminus for affinity purification of the heterologous protein using Glutathione Sepharose 4B beads (Amersham Biosciences). The sequence of the cloned expression vector was verified by DNA sequencing, and was used as a template to attach yeast cytosine deaminase gene (yCD) to express GST-TSGLink-yCD protein.

The expression vector was introduced into *E. coli*; and expression of the chimeric protein was induced with IPTG (isopropyl-beta-D-thiogalactopyranoside). Bacteria were lysed, and the soluble fraction and insoluble pellet were analyzed for the presence of the chimeric protein. GST-fusion protein in the soluble fraction was performed according to the manufacturer's instructions (Amersham Biosciences). Most of the expressed GST-fusion protein was found in the insoluble pellet fraction of *E.coli* lysate.

Example 4

Construction of *E.coli* Expression Vector for $His_6$-tagged TSG6Link-yCD Fusion Protein with a $[Gly_4Ser]_3$ Flexible Linker Between TSG6Link and yCD pET41a expression vector was digested with Nde I and Xho I to remove the GST gene and insert a 6x histidine residue ($His_6$), an affinity tag for protein purification. yCD gene was amplified by PCR using a 5'-primer linker containing nucleotide sequence providing for an Nde I site and encoding $[Gly_4Ser]_3$. The $[Gly_4Ser]_3$-yCD gene was ligated into the pET41a vector. TSG6Link gene was amplified by PCR using a 5'-primer linker containing nucleotide sequence of $His_6$ and a thrombin cleavage recognition sequence (LVPRGS), and the PCR amplified DNA was ligated into Nde I restriction site of $[Gly_4Ser]_3$-yCD gene in pET41a expression vector. The nucleotide sequence of the insert was verified, and the expression vector was transformed into BL21-Codon Plus (DE3)-RIPL *E.coli* (Stratagene) for protein expression.

The $His_6$-tagged TSG6Link-$[Gly_4Ser]_3$-yCD (HTY) chimeric fusion protein expression was induced with IPTG when $OD_{600\ nm}$ cell culture reached about 0.6, and the culture was incubated at room temperature for overnight. The bacterial cells were centrifuged and resuspended in the lysis buffer containing protease inhibitor phenylmethylsulfonyl fluoride (PMSF), and lysed by a freeze-thaw cycle followed by lysozyme treatment and sonication. The cell lysate was centrifuged at 10,000×g for 45 min at 4° C. to separate soluble and insoluble fractions. The HTY fusion protein was purified from the soluble fraction using HisTrapp FF column (Amersham Biosciences) according to the manufacturer's instructions.

Figure 9:
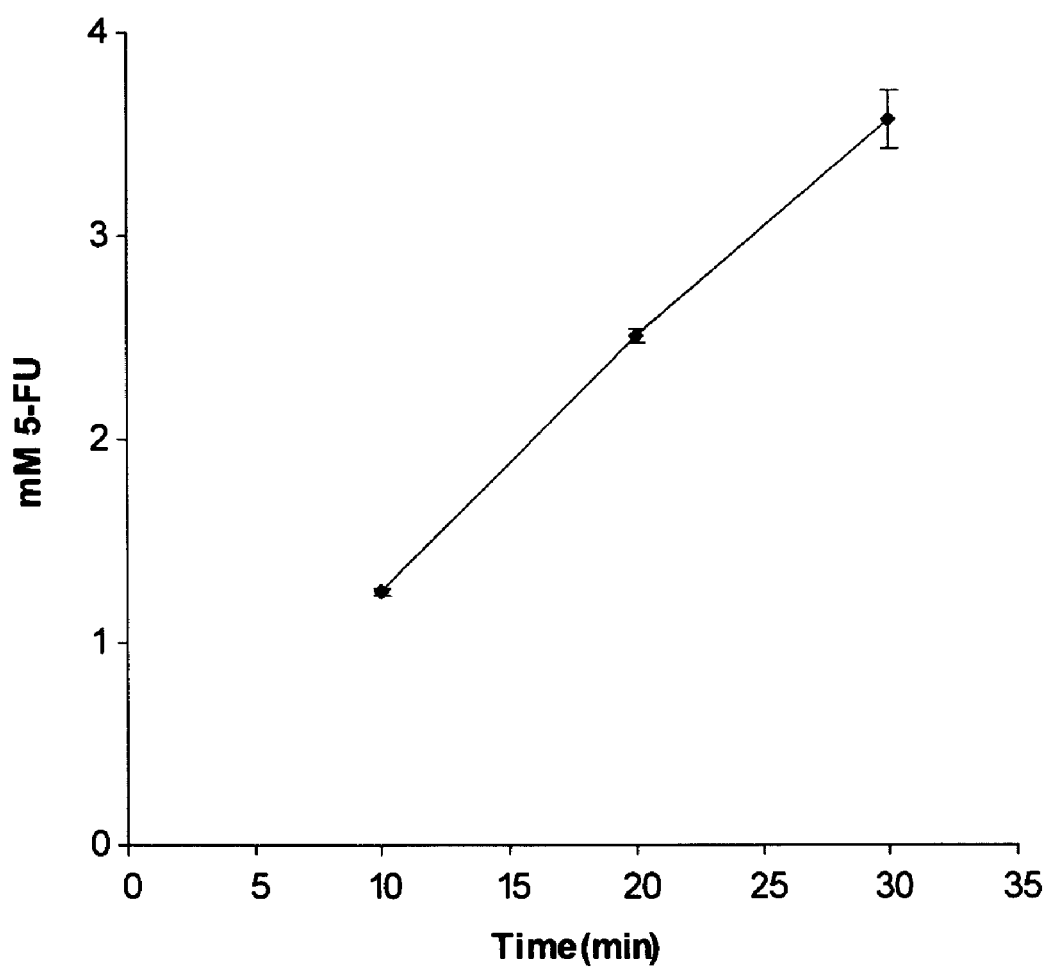
FIG. 9 depicts conversion of 5-FC to 5-FU by HTY.

As shown in FIG. 9, the HTY chimeric fusion protein can also convert 5-FC into 5-FU. The reaction was carried out in 2× phosphate buffered saline (PBS) at 37° C. The reaction mixture contained 5 mM 5-FC and 10 µg HTY in 1 ml total volume. At each time point (10 minutes, 20 minutes, and 30 minutes), 20 μl reaction mixture was diluted to 1 ml 1× PBS containing 0.1 N HCl. The concentration of 5-FU was measured by UV absorbance at 255 nm and 290 nm, as described. Senter et al. 1991.

Example 5

Figure 10:
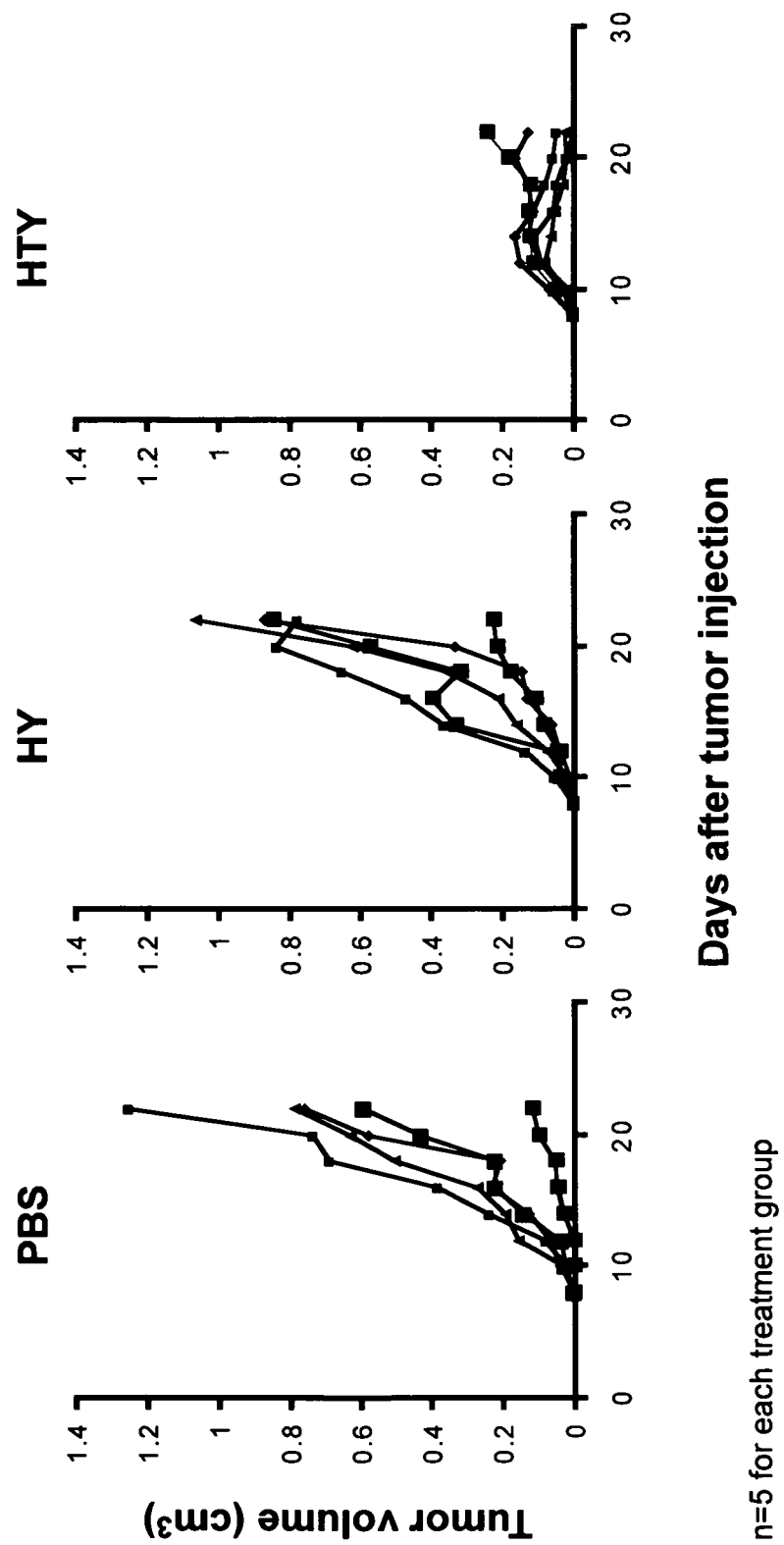
FIG. 10 depicts C26 tumor growth following administration of PBS, HY, or HTY.
Figure 11:
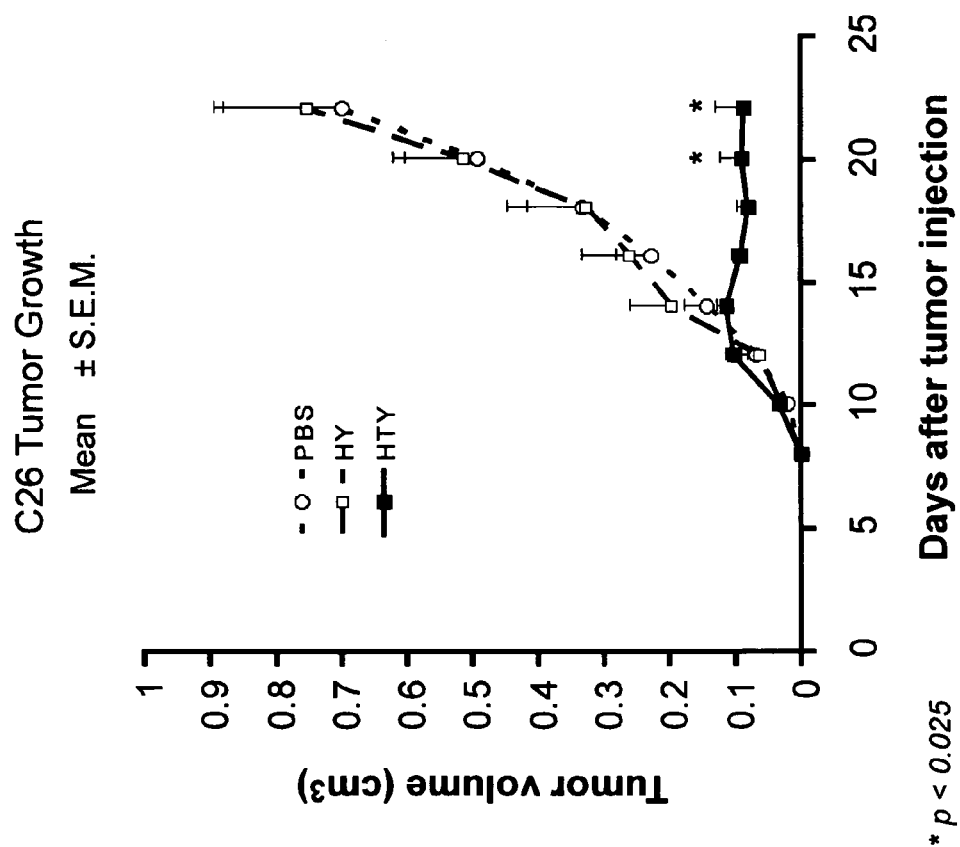
FIG. 11 depicts C26 tumor growth following administration of PBS, HY, or HTY.
Figure 12:
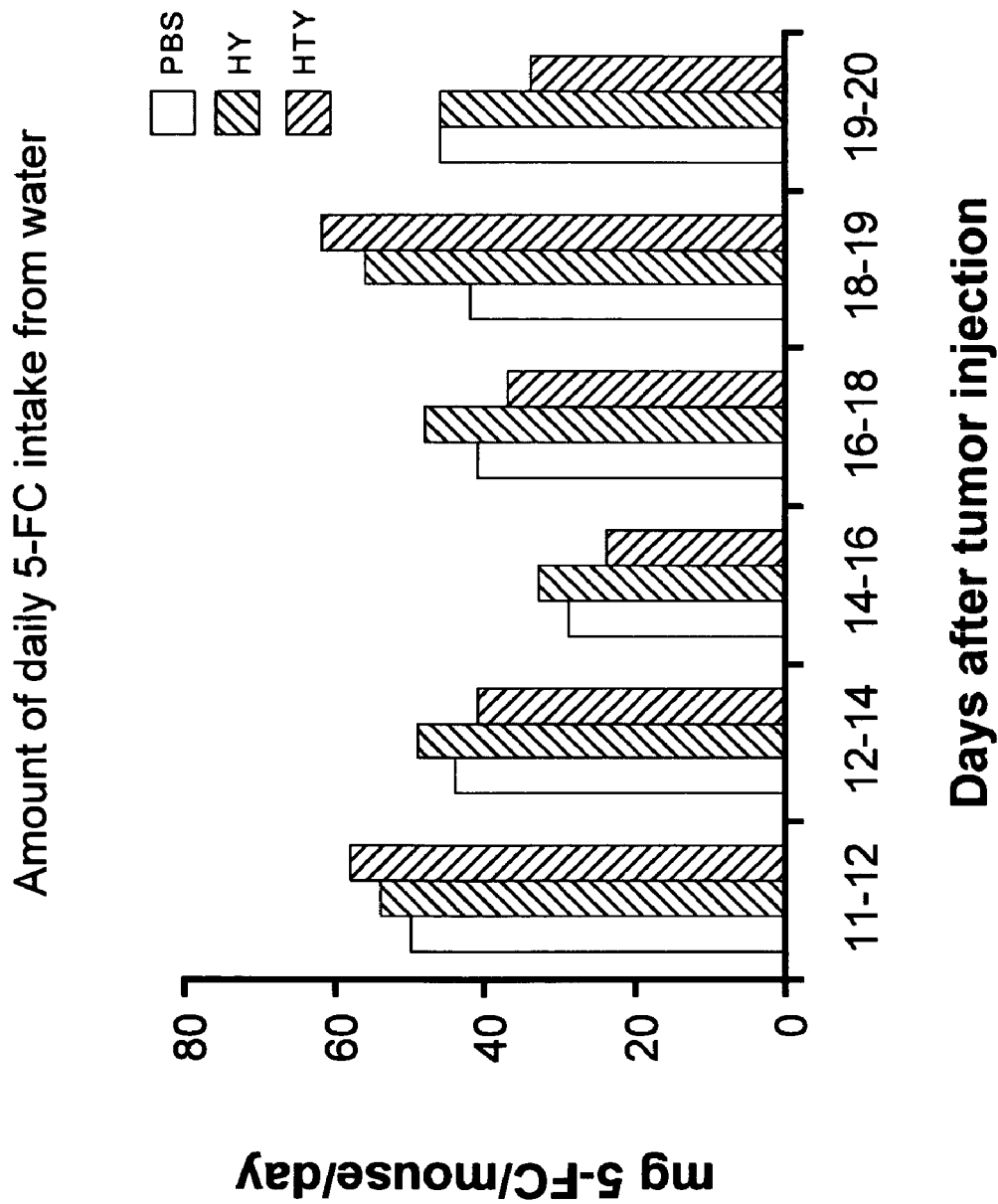
FIG. 12 depicts the amount of daily 5-FC intake from water.

In Vivo Anti-tumor Experiment Using His-tagged TSG6Link-[Gly$_4$Ser]$_3$-yCD Chimeric Fusion Protein on C26 Tumor Mice C26 murine colon adenocarcinoma cells were injected ($4\times10^5$ cells in 50 μl volume of cell media) s.c. to the right hind flank of 6 to 8-week old BALB/c female mice on Day 0. On Day 12, 0.2 unit (1 unit is equal to 1 μmol 5-FU formed/min) of either HTY or HY (Histidine tag-cytosine deaminase without TSG6) was injected to each mouse at the site of tumor in 80 μl (5 mice for each treatment group), and water containing 10 mg/ml 5-FC was given to each treatment group. On Day 14, the second dose (0.6 unit) of either HTY or HY was given to each mouse. For the control group, the same volume of 1× PBS was injected for both days. The tumor size and 5-FC water intake were measured every 2 days. Although the 5-FC intake from water fluctuated from 24 mg to 58 mg/day/mouse, the daily intake was similar among the three treatment groups. The results are shown in FIGS. 10-12. The initial animal study indicates that a combination of 5-FC/HTY treatment has a statistically significant anti-tumor effect compared to 5-FC/HY ($p<0.020$) and 5-FC/PBS treatments ($p<0.025$) on Day 20. There is no significant difference between 5-FC/PBS and 5-FC/HY treatment groups. ANOVA and Tukey tests are performed for statistical analysis.

Example 6

In Vivo Anti-Tumor Effect of 5-FC on HBD-yCD Fusion Protein Expressing Tumor Cells in SCID Mice To examine whether expressing secreted fusion protein (secHBD-yCD) has superior anti-tumor effect than non-secreted version (matHBD-yCD) in combination with 5-FC treatment, the nucleotide sequence encoding the N-terminal secretion signal peptide of CD44 is removed in matHBD-yCD construct. Mammalian expression vector (pcDNA4/TO/MycHisA, Invitrogen) containing either secHBD-yCD or matHBD-yCD was constructed and the sequences were verified. Also, point mutants were made to express the fusion protein that lack hyaluronan-binding activity. All these variants of HBD-yCD are amplified by PCR and ligated into adenovirus vector for viral delivery of the fusion gene.

Human breast tumor model described in Example 2 is used to examine the in vivo anti-tumor effect of 5-FC on sec/matHBD-yCD expressing tumor. secHBD-yCD or matHBD-yCD fusion gene is delivered to the breast tumor cells via either viral or non-viral gene delivery methods (e.g., adenovirus vector, or mammalian expression vector encapsulated in nano-lipid particles, polymer, electroporation, or hydrodynamic delivery). The fusion protein expressing DNA with an appropriate gene carrier is injected directly at the site of tumor to transfect the tumor cells. Alternatively, polymer-DNA complex is injected to tail-vein of the mice to target and transfect tumor cells. Tumor bearing mice are given 5-FC containing water (10 mg/ml) daily. The tumor size and the amount of 5-FC intake are monitored every 2 days. The group receiving the construct with a plasmid that drives expression of the secreted fusion protein (secHBD-yCD) is predicted to display a better response to the 5-FC treatment than will the matHBD-yCD or fusion protein that lack functional matrix attachment component.

REFERENCES

Ahrens, T., et. al., Soluble CD44 inhibits melanoma tumor growth by blocking cell surface CD44 binding to hyaluronan. Oncogene (2001) 20: 3399-3408

Allen, T. M., Ligand-targeted therapeutics in anticancer therapy. Nature Cancer Rev. (2002) 2:750-763

Allen, T. M. and Cullis, P. R., Drug delivery systems: entering the mainstream. Science (2004) 303:1818-1822

Anttila, M. A., et. al., High levels of stromal hyaluronan predict poor disease outcome in epithelial ovarian cancer. Cancer Res. (2000) 60:150-155

Auvinen, P., et. al., Hyaluronan in peritumoral stroma and malignant cells associates with breast cancer spreading and predicts survival. Am. J. Pathol. (2000) 156:529-536

Bajorath, J. et. al., Identification of CD44 residues important for hyaluronan binding and delineation of the binding sites. J. Biol. Chem. (1998) 273:338-343

Banerji, S. et. al., Characterization of a functional hyaluronan-binding domain from the human CD44 molecule expressed in *Escherichia coli*. Protein Expr. and Purif. (1998) 14:371-381

Dakappagari, N. K., et. al., Prevention of mammary tumors with a chimeric HER-2 B-cell epitope peptide vaccine. Cancer Res. (2000) 60:3782-3789

Day, A. J., and Prestwich, G. D., Hyaluronan-binding proteins: tying up the giant. J. Biol. Chem. (2002) 277:4585-4588

Fraser, J. R., Laurent, T. C., and Laurent, U. B., Hyalrunonan: its nature, distribution, functions and turnover. J. Intern. Med. (1997) 242:27-33

Heidelberger, C., et. al. Fluorinated pyrimidines. A new class of tumor inhibitory compounds. Nature (1957) 179:663-666

Itano, N., et.al., Relationship between hyaluronan production and metastatic potential of mouse mammary carcinoma cells. Cancer Res. (1999) 59:2499-2504

Jojovic, M., et. al., Expression of hyaluronate and hyaluronate synthase in human primary tumors and their metastases in scid mice. Cancer Letters (2002) 188:181-189

Kievit, E., et. al., Superiority of yeast over bacterial cytosine deaminase for enzyme/prodrug gene therapy in colon cancer xenographts. Cancer Res. (1999) 59:1417-1421

Kosaki, R., Watanabe, J., Yamaguchi, Y., Overproduction of HA by expression of hyaluronan synthase Has2 enhances anchorage-independent growth and tumorigenicity. Cancer Res (1999) 59:1141-11145

Leonetti, C. et. al., In vivo administration of liposomal vincristine sensitizes drug-resistant human solid tumors. Int. J. Cancer (2004) 110:767-774

Miyagi, T., et. al., Gene therapy for prostate cancer using the cytosine deaminase/uracil phosphoribosyltransferase suicide system. J. Gene Med. (2003) 5:30-37

Mummert M E, Mohamadzadeh M, Mummert D I, Mizumoto N, and Takashima A. Development of a peptide inhibitor of hyaluronan-mediated leukocyte trafficking. J. Exp. Med. 192:769-779, 2000.

Park, J. W., et. al., Tumor targeting using anti-her2 immunoliposomes. J. Control. Release (2001) 95-113

Peterson, R. M., et. al., Perturbation of hyaluronan interactions by soluble CD44 inhibits growth of murine mammary carcinoma cells in ascites. Am. J. Pathol. (2000) 156:2159-2167

Senter, P. D., et. al., Generation of 5-fluorouracil from 5-fluorocytosine by monoclonal antibody-cytosine deaminase conjugates. Bioconj. Chem. (1991) 2:447-451

Spicer, A. P., Augustine, M. L., and McDonald, J. A., Molecular cloning and characterization of a putative mouse hyaluronan synthase. J. Biol. Chem. (1996) 271: 23400-23406

Stem, R. Hyaluronan degradation in tumor growth and metastasis. Trend. Glycosci. Glytotechnol. (2004) 16:181-195

Subbaramaiah, K. et. al., Cyclooxygenase-2 is overexpressed in HER-2/neu-positive breast cancer. J. Biol. Chem. (2002) 277:18649-18657

Teriete, P., et. al., Structure of the regulatory hyaluronan binding domain in the inflammatory leukocyte homing receptor CD44. Molec. Cell (2004) 13:483-496

Toole, B. Hyaluronan: from extracellular glue to pericellular cue. Nat. Rev. Cancer (2004) 4:528-539

Torano, J. S., Vermes, A., and Guschelaar, H-J, Simultaneous determination of flucytosine and fluorouracil in human plasma by high-performance liquid chromatography. Biomed. Chromatogr. (2001) 15:89-94

Wallace, P. D., et. al., Intratumoral generation of 5-fluorouracil mediated by an antibody-cytosine deaminase conjuage in combination with 5-fluorocytosine. Cancer Res. (1994) 54:2719-2723

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A fusion polypeptide comprising a hyaluronan-binding polypeptide fused to a heterologous polypeptide, wherein said hyaluronan-binding polypeptide consists of the amino acid sequence of SEQ ID NO:2.

2. The fusion polypeptide of claim 1, wherein the heterologous polypeptide is a growth factor, an enzyme that activates a prodrug, an angiogenesis inhibitor, a chemoattractant polypeptide or a matrix metalloproteinase inhibitor.

3. The fusion polypeptide of claim 2, wherein the growth factor is a growth factor selected from nerve growth factor, vascular endothelial growth factor, acid fibroblast growth factor, basic fibroblast growth factor, ciliary neurotrophic factor, brain derived neurotrophic factor, neurotrophin-3, epidermal growth factor, transforming growth factor-α, transforming growth factor-β, neurotrophin-4, GM-CSF, G-CSF, stromal derived factor-1, a bone morphogenetic protein, cardiotrophin-1, choline acetyltransferase development factor, oncostatin M, glial cell-line-derived neurotrophic factor, insulin, insulin-like growth factor-1, insulin-like growth factor-2, interleukin-6, leukemia inhibitor factor, neurite promoting factor, platelet-derived growth factor, protease nexin-1, S-100, transforming growth factor-β, and vasoactive intestinal peptide.

4. The polypeptide of claim 1, wherein the heterologous polypeptide is selected from IL-2, IFN-α, IL-8, IFN-γ, IL-12, and IFN-β.

5. The fusion polypeptide of claim 2, wherein the enzyme that activates a prodrug is cytosine deaminase.

6. A composition comprising the fusion polypeptide of claim 1 and a buffer.

7. A composition comprising: a) the fusion polypeptide of claim 1; and b) a pharmaceutically acceptable excipient.

8. The composition of claim 7, wherein the composition further comprises a cancer chemotherapeutic agent.

* * * * *